US012734341B2

(12) United States Patent
Urbanski et al.

(10) Patent No.: US 12,734,341 B2
(45) Date of Patent: Sep. 15, 2026

(54) MEDICAL GUIDEWIRE ASSEMBLY HAVING PREDETERMINED SPATIAL GEOMETRY

(71) Applicant: Boston Scientific Medical Device Limited, Ballybrit (IE)

(72) Inventors: John Paul Urbanski, Toronto (CA); Christian Balkovec, Burlington (CA)

(73) Assignee: Boston Scientific Medical Device Limited, Galway (IE)

(*) Notice: Subject to any disclaimer, the term of this patent is extended or adjusted under 35 U.S.C. 154(b) by 1014 days.

(21) Appl. No.: 17/793,079

(22) PCT Filed: Jan. 27, 2021

(86) PCT No.: PCT/IB2021/050623
§ 371 (c)(1),
(2) Date: Jul. 15, 2022

(87) PCT Pub. No.: WO2021/152474
PCT Pub. Date: Aug. 5, 2021

(65) Prior Publication Data

US 2023/0042352 A1 Feb. 9, 2023

Related U.S. Application Data

(60) Provisional application No. 62/967,194, filed on Jan. 29, 2020.

(51) Int. Cl.
*A61M 25/09* (2006.01)

(52) U.S. Cl.
CPC ................ *A61M 25/09041* (2013.01); *A61M 2025/09075* (2013.01); *A61M 2025/09125* (2013.01); *A61M 2210/125* (2013.01)

(58) Field of Classification Search
CPC .. A61M 25/09041; A61M 2025/09075; A61M 2025/09125; A61M 2010/125
See application file for complete search history.

(56) References Cited

U.S. PATENT DOCUMENTS

| | | | |
|---|---|---|---|
| 175,254 | A | 3/1876 | Oberly |
| 827,626 | A | 7/1906 | Gillet |

(Continued)

FOREIGN PATENT DOCUMENTS

| | | | |
|---|---|---|---|
| EP | 2908735 | B1 | 3/2019 |
| EP | 2566558 | B1 | 4/2019 |

(Continued)

OTHER PUBLICATIONS

International Search Report and Written Opinion received for PCT Patent Application No. PCT/IB2021/050623, mailed on Apr. 23, 2021, 10 pages.

*Primary Examiner* — Edelmira Bosques
(74) *Attorney, Agent, or Firm* — Nelson Mullins Riley & Scarborough LLP

(57) ABSTRACT

Medical guidewire assembly is movable through guidewire introducer positionable proximate to a biological wall located within the body of a patient. Medical guidewire assembly has flexible distal shaft section configured to extend along the guidewire introducer. Medical guidewire assembly has a predetermined spatial geometry once the flexible distal shaft section is removed from guidewire introducer. Medical guidewire assembly also has a piercing stylet device configured to puncture the biological wall in response to placement of guidewire introducer (in use) proximate to the biological wall, and movement of the flexible distal shaft section through the guidewire introducer. The predetermined spatial geometry is configured to prevent physical contact between the piercing stylet device and adjacently positioned tissue of the patient in response to formation of the predetermined spatial geometry.

20 Claims, 8 Drawing Sheets

(56) References Cited

U.S. PATENT DOCUMENTS 848,711 A 4/1907 Daniel
1,072,954 A 9/1913 Junn
1,279,654 A 9/1918 Charlesworth
1,918,094 A 7/1933 Geekas
1,996,986 A 4/1935 Weinberg
2,021,989 A 11/1935 De Master
2,146,636 A 2/1939 Lipchow
3,429,574 A 2/1969 Williams
3,448,739 A 6/1969 Stark et al.
3,575,415 A 4/1971 Fulp et al.
3,595,239 A 7/1971 Petersen
4,129,129 A 12/1978 Amrine
4,244,362 A 1/1981 Anderson
4,401,124 A 8/1983 Guess et al.
4,639,252 A 1/1987 Kelly et al.
4,641,649 A 2/1987 Walinsky et al.
4,669,467 A 6/1987 Willett et al.
4,682,596 A 7/1987 Bales et al.
4,790,311 A 12/1988 Ruiz
4,790,809 A 12/1988 Kuntz
4,793,350 A 12/1988 Mar et al.
4,807,620 A 2/1989 Strul et al.
4,832,048 A 5/1989 Cohen
4,840,622 A 6/1989 Hardy
4,863,441 A 9/1989 Lindsay et al.
4,884,567 A 12/1989 Elliott et al.
4,892,104 A 1/1990 To et al.
4,896,671 A 1/1990 Cunningham et al.
4,928,693 A 5/1990 Goodin et al.
4,936,281 A 6/1990 Stasz
4,960,410 A 10/1990 Pinchuk
4,977,897 A 12/1990 Hurwitz
4,998,933 A 3/1991 Eggers et al.
5,006,119 A 4/1991 Acker et al.
5,019,076 A 5/1991 Yamanashi et al.
5,047,026 A 9/1991 Rydell
5,081,997 A 1/1992 Bosley et al.
5,098,431 A 3/1992 Rydell
5,112,048 A 5/1992 Kienle
5,154,724 A 10/1992 Andrews
5,201,756 A 4/1993 Horzewski et al.
5,209,741 A 5/1993 Spaeth
5,211,183 A 5/1993 Wilson
5,221,256 A 6/1993 Mahurkar
5,230,349 A 7/1993 Langberg
5,281,216 A 1/1994 Klicek
5,300,068 A 4/1994 Rosar et al.
5,300,069 A 4/1994 Hunsberger et al.
5,314,418 A 5/1994 Takano et al.
5,318,525 A 6/1994 West et al.
5,327,905 A 7/1994 Avitall
5,364,393 A 11/1994 Auth et al.
5,372,596 A 12/1994 Klicek et al.
5,380,304 A 1/1995 Parker
5,397,304 A 3/1995 Truckai
5,403,338 A 4/1995 Milo
5,423,809 A 6/1995 Klicek
5,425,382 A 6/1995 Golden et al.
5,490,859 A 2/1996 Mische et al.
5,497,774 A 3/1996 Swartz et al.
5,507,751 A 4/1996 Goode et al.
5,509,411 A 4/1996 Littmann et al.
5,540,681 A 7/1996 Strul et al.
5,545,200 A 8/1996 West et al.
5,555,618 A 9/1996 Winkler
5,571,088 A 11/1996 Lennox et al.
5,575,766 A 11/1996 Swartz et al.
5,575,772 A 11/1996 Lennox
5,599,347 A 2/1997 Hart et al.
5,605,162 A 2/1997 Mirzaee et al.
5,617,878 A 4/1997 Taheri
5,622,169 A 4/1997 Golden et al.
5,624,430 A 4/1997 Eton et al.
5,667,488 A 9/1997 Lundquist et al.
5,673,695 A 10/1997 Mcgee et al.
5,674,208 A 10/1997 Berg et al.
5,683,366 A 11/1997 Eggers et al.
5,720,744 A 2/1998 Eggleston et al.
5,722,425 A 3/1998 Mats
5,741,249 A 4/1998 Moss et al.
5,766,135 A 6/1998 Terwilliger
5,779,688 A 7/1998 Imran et al.
5,810,764 A 9/1998 Eggers et al.
5,814,028 A 9/1998 Swartz et al.
5,830,214 A 11/1998 Flom et al.
5,836,875 A 11/1998 Webster, Jr.
5,849,011 A 12/1998 Jones et al.
5,851,210 A 12/1998 Torossian
5,885,227 A 3/1999 Finlayson
5,888,201 A 3/1999 Stinson et al.
5,893,848 A 4/1999 Negus et al.
5,893,885 A 4/1999 Webster, Jr.
5,904,679 A 5/1999 Clayman
5,916,210 A 6/1999 Winston
5,921,957 A 7/1999 Killion et al.
5,931,818 A 8/1999 Werp et al.
5,944,023 A 8/1999 Johnson et al.
5,951,482 A 9/1999 Winston et al.
5,957,842 A 9/1999 Littmann et al.
5,964,757 A 10/1999 Ponzi
5,967,976 A 10/1999 Larsen et al.
5,989,276 A 11/1999 Houser et al.
6,007,555 A 12/1999 Devine
6,009,877 A 1/2000 Edwards
6,013,072 A 1/2000 Winston et al.
6,017,340 A 1/2000 Cassidy et al.
6,018,676 A 1/2000 Davis et al.
6,030,380 A 2/2000 Auth et al.
6,032,674 A 3/2000 Eggers et al.
6,048,349 A 4/2000 Winston et al.
6,053,870 A 4/2000 Fulton, III
6,053,904 A 4/2000 Scribner et al.
6,056,747 A 5/2000 Saadat et al.
6,063,093 A 5/2000 Winston et al.
6,093,185 A 7/2000 Ellis et al.
6,106,515 A 8/2000 Winston et al.
6,106,520 A 8/2000 Laufer et al.
6,117,131 A 9/2000 Taylor
6,142,992 A 11/2000 Cheng et al.
6,146,380 A 11/2000 Racz et al.
6,155,264 A 12/2000 Ressemann et al.
6,156,031 A 12/2000 Aita et al.
6,171,305 B1 1/2001 Sherman
6,179,824 B1 1/2001 Eggers et al.
6,193,676 B1 2/2001 Winston et al.
6,193,715 B1 2/2001 Wrublewski et al.
6,210,408 B1 4/2001 Chandrasekaran et al.
6,217,575 B1 4/2001 Devore et al.
6,221,061 B1 4/2001 Engelson et al.
6,228,076 B1 5/2001 Winston et al.
6,245,054 B1 6/2001 Fuimaono et al.
6,267,758 B1 7/2001 Daw et al.
6,283,983 B1 9/2001 Makower et al.
6,292,678 B1 9/2001 Hall et al.
6,293,945 B1 9/2001 Parins et al.
6,296,615 B1 10/2001 Brockway et al.
6,296,636 B1 10/2001 Cheng et al.
6,302,898 B1 10/2001 Edwards et al.
6,304,769 B1 10/2001 Arenson et al.
6,315,777 B1 11/2001 Comben
6,328,699 B1 12/2001 Eigler et al.
6,360,128 B2 3/2002 Kordis et al.
6,364,877 B1 4/2002 Goble et al.
6,385,472 B1 5/2002 Hall et al.
6,394,976 B1 5/2002 Winston et al.
6,395,002 B1 5/2002 Ellman et al.
6,419,674 B1 7/2002 Bowser et al.
6,428,551 B1 8/2002 Hall et al.
6,450,989 B2 9/2002 Dubrul et al.
6,475,214 B1 11/2002 Moaddeb
6,485,485 B1 11/2002 Winston et al.
6,508,754 B1 1/2003 Liprie et al.
6,524,303 B1 2/2003 Garibaldi
6,530,923 B1 3/2003 Dubrul et al.

(56) References Cited

U.S. PATENT DOCUMENTS 6,554,827 B2 4/2003 Chandrasekaran et al.
6,562,031 B2 5/2003 Chandrasekaran et al.
6,562,049 B1 5/2003 Norlander et al.
6,565,562 B1 5/2003 Shah et al.
6,607,529 B1 8/2003 Jones et al.
6,632,222 B1 10/2003 Edwards et al.
6,639,999 B1 10/2003 Cookingham et al.
6,650,923 B1 11/2003 Lesh et al.
6,651,672 B2 11/2003 Roth
6,662,034 B2 12/2003 Segner et al.
6,663,621 B1 12/2003 Winston et al.
6,702,811 B2 3/2004 Stewart et al.
6,709,444 B1 3/2004 Makower
6,723,052 B2 4/2004 Mills
6,733,511 B2 5/2004 Hall et al.
6,740,103 B2 5/2004 Hall et al.
6,752,800 B1 6/2004 Winston et al.
6,755,816 B2 6/2004 Ritter et al.
6,811,544 B2 11/2004 Schaer
6,814,733 B2 11/2004 Schwartz et al.
6,820,614 B2 11/2004 Bonutti
6,834,201 B2 12/2004 Gillies et al.
6,842,639 B1 1/2005 Winston et al.
6,852,109 B2 2/2005 Winston et al.
6,855,143 B2 2/2005 Davison et al.
6,860,856 B2 3/2005 Ward et al.
6,869,431 B2 3/2005 Maguire et al.
6,911,026 B1 6/2005 Hall et al.
6,951,554 B2 10/2005 Johansen et al.
6,951,555 B1 10/2005 Suresh et al.
6,955,675 B2 10/2005 Jain
6,970,732 B2 11/2005 Winston et al.
6,980,843 B2 12/2005 Eng et al.
7,029,470 B2 4/2006 Francischelli et al.
7,056,294 B2 6/2006 Khairkhahan et al.
7,083,566 B2 8/2006 Tornes et al.
7,112,197 B2 9/2006 Hartley et al.
7,335,197 B2 2/2008 Sage et al.
7,618,430 B2 11/2009 Scheib
7,651,492 B2 1/2010 Wham
7,666,203 B2 2/2010 Chanduszko et al.
7,678,081 B2 3/2010 Whiting et al.
7,682,360 B2 3/2010 Guerra
7,828,796 B2 11/2010 Wong et al.
7,900,928 B2 3/2011 Held et al.
8,192,425 B2 6/2012 Mirza et al.
8,257,323 B2 9/2012 Joseph et al.
8,388,549 B2 3/2013 Paul et al.
8,500,697 B2 8/2013 Kurth et al.
8,517,959 B2 8/2013 Kurosawa et al.
9,314,595 B2 * 4/2016 Gurley .................... A61B 6/12
11,339,579 B1 5/2022 Stearns
2001/0012934 A1 8/2001 Chandrasekaran et al.
2001/0021867 A1 9/2001 Kordis et al.
2002/0019644 A1 2/2002 Hastings et al.
2002/0022781 A1 2/2002 McIntire et al.
2002/0022836 A1 2/2002 Goble et al.
2002/0035361 A1 3/2002 Houser et al.
2002/0087153 A1 7/2002 Roschak et al.
2002/0087156 A1 7/2002 Maguire et al.
2002/0111618 A1 8/2002 Stewart et al.
2002/0123749 A1 9/2002 Jain
2002/0147485 A1 10/2002 Mamo et al.
2002/0169377 A1 11/2002 Khairkhahan et al.
2002/0188302 A1 12/2002 Berg et al.
2002/0198521 A1 12/2002 Maguire
2003/0032929 A1 2/2003 Mcguckin
2003/0040742 A1 2/2003 Underwood et al.
2003/0144658 A1 7/2003 Schwartz et al.
2003/0158480 A1 8/2003 Tornes et al.
2003/0163153 A1 8/2003 Scheib
2003/0225392 A1 12/2003 Mcmichael et al.
2004/0015162 A1 1/2004 Mcgaffigan
2004/0024396 A1 2/2004 Eggers
2004/0030328 A1 2/2004 Eggers et al.
2004/0044350 A1 3/2004 Martin et al.
2004/0073243 A1 4/2004 Sepetka et al.
2004/0077948 A1 4/2004 Violante et al.
2004/0116851 A1 6/2004 Johansen et al.
2004/0127963 A1 7/2004 Uchida et al.
2004/0133113 A1 7/2004 Krishnan
2004/0133130 A1 7/2004 Ferry et al.
2004/0143256 A1 7/2004 Bednarek
2004/0147950 A1 7/2004 Mueller et al.
2004/0181213 A1 9/2004 Gondo
2004/0230188 A1 11/2004 Cioanta et al.
2005/0004585 A1 1/2005 Hall et al.
2005/0010208 A1 1/2005 Winston et al.
2005/0049628 A1 3/2005 Schweikert et al.
2005/0059966 A1 3/2005 Mcclurken et al.
2005/0065507 A1 3/2005 Hartley et al.
2005/0085806 A1 4/2005 Auge et al.
2005/0096529 A1 5/2005 Cooper et al.
2005/0101984 A1 5/2005 Chanduszko et al.
2005/0119556 A1 6/2005 Gillies et al.
2005/0137527 A1 6/2005 Kunin
2005/0149012 A1 7/2005 Penny et al.
2005/0203504 A1 9/2005 Wham et al.
2005/0203507 A1 9/2005 Truckai et al.
2005/0261607 A1 11/2005 Johansen et al.
2005/0288631 A1 12/2005 Lewis et al.
2006/0041253 A1 2/2006 Newton et al.
2006/0074398 A1 4/2006 Whiting et al.
2006/0079769 A1 4/2006 Whiting et al.
2006/0079787 A1 4/2006 Whiting et al.
2006/0079884 A1 4/2006 Manzo et al.
2006/0085054 A1 4/2006 Zikorus et al.
2006/0089638 A1 4/2006 Carmel et al.
2006/0106375 A1 5/2006 Werneth et al.
2006/0135962 A1 6/2006 Kick et al.
2006/0142756 A1 6/2006 Davies et al.
2006/0189972 A1 8/2006 Grossman
2006/0241586 A1 10/2006 Wilk
2006/0247672 A1 11/2006 Vidlund et al.
2006/0264927 A1 11/2006 Ryan
2006/0276710 A1 12/2006 Krishnan
2007/0060879 A1 3/2007 Weitzner et al.
2007/0066975 A1 3/2007 Wong et al.
2007/0118099 A1 5/2007 Trout, III
2007/0123964 A1 5/2007 Davies et al.
2007/0167775 A1 7/2007 Kochavi et al.
2007/0208256 A1 9/2007 Marilla
2007/0225681 A1 9/2007 House
2007/0270791 A1 11/2007 Wang et al.
2008/0039865 A1 2/2008 Shaher et al.
2008/0042360 A1 2/2008 Veikley
2008/0086120 A1 4/2008 Mirza et al.
2008/0097213 A1 4/2008 Carlson et al.
2008/0108987 A1 5/2008 Bruszewski et al.
2008/0146918 A1 6/2008 Magnin et al.
2008/0171934 A1 7/2008 Greenan et al.
2008/0208121 A1 8/2008 Youssef et al.
2008/0275439 A1 11/2008 Francischelli et al.
2009/0105742 A1 4/2009 Kurth et al.
2009/0138009 A1 5/2009 Viswanathan et al.
2009/0163850 A1 6/2009 Betts et al.
2009/0177114 A1 7/2009 Chin et al.
2009/0264977 A1 10/2009 Bruszewski et al.
2010/0087789 A1 4/2010 Leeflang et al.
2010/0125282 A1 5/2010 Machek et al.
2010/0168684 A1 7/2010 Ryan
2010/0179632 A1 7/2010 Bruszewski et al.
2010/0191142 A1 7/2010 Paul et al.
2010/0194047 A1 8/2010 Sauerwine
2011/0046619 A1 2/2011 Ducharme
2011/0152716 A1 6/2011 Chudzik et al.
2011/0160592 A1 6/2011 Mitchell
2011/0190763 A1 8/2011 Urban et al.
2012/0232546 A1 9/2012 Mirza et al.
2012/0265055 A1 10/2012 Melsheimer et al.
2012/0330156 A1 12/2012 Brown et al.
2013/0184551 A1 7/2013 Paganelli et al.
2013/0184735 A1 7/2013 Fischell et al.
2013/0282084 A1 10/2013 Mathur et al.

(56) References Cited

U.S. PATENT DOCUMENTS

| | | | | |
|---|---|---|---|---|
| 2014/0114254 | A1 | 4/2014 | Irwin et al. | |
| 2014/0206987 | A1 | 7/2014 | Urbanski et al. | |
| 2014/0296769 | A1 | 10/2014 | Hyde et al. | |
| 2016/0000501 | A1* | 1/2016 | Davies | A61B 18/1492<br>606/41 |
| 2016/0220741 | A1 | 8/2016 | Garrison et al. | |
| 2019/0021763 | A1 | 1/2019 | Zhou et al. | |
| 2019/0167305 | A1* | 6/2019 | Pedersen | A61B 17/3468 |
| 2019/0247035 | A1 | 8/2019 | Gittard et al. | |

FOREIGN PATENT DOCUMENTS

| | | | |
|---|---|---|---|
| JP | 09-173463 | A | 7/1997 |
| WO | 2011/140177 | A1 | 11/2011 |
| WO | 2018/181520 | A1 | 10/2018 |
| WO | 2019/113043 | A1 | 6/2019 |

* cited by examiner 906
102
802
907
903
902
104
100
904
905
900

906
800
104
902
903
904
100
900
905

MEDICAL GUIDEWIRE ASSEMBLY HAVING PREDETERMINED SPATIAL GEOMETRY

TECHNICAL FIELD

This document relates to the technical field of (and is not limited to) a medical guidewire assembly including a flexible distal shaft section configured to have a predetermined spatial geometry (preferably once the flexible distal shaft section is moved beyond an exit portal of a guidewire introducer); more specifically (and not limited thereto), the predetermined spatial geometry, once formed, is configured to prevent physical contact between a piercing stylet device (of the medical guidewire assembly) and the adjacently positioned tissue of a patient (and method therefor).

BACKGROUND

Known medical devices, such as a medical guidewire assembly, are configured to facilitate a medical procedure, and help healthcare providers diagnose and/or treat medical conditions of patients.

SUMMARY

It will be appreciated that there exists a need to mitigate (at least in part) at least one problem associated with the existing medical guidewire assemblies (also called the existing technology). After much study of, and experimentation with, the existing medical guidewire assemblies, an understanding (at least in part) of the problem and its solution have been identified (at least in part) and are articulated (at least in part) as follows:

The heart septum is a dividing wall (a biological wall) positioned between the right side and the left side of the heart of a patient. The portion of the septum that separates the right atria and the left atria of the heart is termed the atrial septum (or interatrial septum), whereas the portion of the septum that lies between the right ventricle and the left ventricle of the heart is called the ventricular septum (or interventricular septum).

Transseptal access is a medical procedure for accessing the left atrium of the heart of a patient. Transseptal access via mechanical means may require piercing the septum with the sharp distal tip (also called a cutting or puncturing tip) of a device. Once positioned in the left atrium, the sharp distal tip may potentially contact adjacently located tissue resulting in inadvertent (unwanted) tissue damage.

Known mechanical transseptal access solutions leave the sharp distal tip exposed (after the septum has been punctured by the sharp distal tip or once the sharp distal tip has been positioned in the tissue, such as in the left atrium of the heart of a patient), which may create a potential risk of inadvertent puncture and/or damage to the adjacently positioned tissue.

Known mechanical puncture systems for transseptal access, particularly those that are guidewire-based, have distal curved geometries that do not control the direction (movement) of the known systems as the known systems (such as, a guidewire) are deployed from (out of) an accessory device (such as, a guidewire introducer). Thus, for the user (the doctor performing the medical procedure), for the case where a sharp distal tip happens to be near sensitive anatomical structures (tissues), not being able to predict with relative certainty where the sharp distal tip of the known mechanical puncture systems might deploy from the accessory device may lead to unwanted or increased procedural complexity and/or may inflict potential harm to the patient.

Known transseptal guidewires include compliant wires with sharp distal tips and a distal curve that forms a "J" shaped formation when relaxed (that is, once the distal tip section becomes unsupported by, or removed from the interior (such as, an elongated interior channel) of the accessory device, or once removed from the interior of the accessory device). While this arrangement may prevent the sharp distal tip from being at the leading end of the guidewire when being manipulated in the left atrium (of the heart), the sharp distal tip may still be able to inadvertently contact tissue in certain instances, such as during device retraction, etc. Further, due to the shape of the curve (relaxed curves) of the distal portions of these guidewires, the direction of deployment may be unpredictable from the accessory devices (the guidewire introducer). It may be uncertain what specific pathway the sharp distal tip may take as the sharp distal tip of the guidewire is deployed in the left atrium of the heart following the puncturing of the septum (the biological wall); this situation or arrangement may lead to unintended puncturing of the tissue.

Known pigtail-shaped guidewires may be commonly used by physicians to secure or anchor their access in the left atrium (of the heart) after the guidewires cross (pass through) the septum via some other means. These types of guidewires may be characterized (identified) by having a distal tip section that is configured to have a distal curved geometry (once removed from the interior of the guidewire introducer or accessory device); the distal curved geometry is configured to wrap around itself in a spiraling curve (a pig tail), and when (once) the distal curved geometry is viewed from the side (along a plane), the distal tip of the distal tip section (of the guidewire) is contained by the spiraling curve. This containment is such that there is no linear displacement vector that may reach along the plane of the spiraling curve that might contact the distal tip extending from the spiraling curve without first contacting another section of the spiraling curve of the guidewire. However, none of these guidewires are configured to mechanically puncture the inter-atrial septum (the biological wall); as a result, the distal tips of these types of devices are blunt (that is, they are not sharp or not made for cutting). These types of guidewires have a tapered core mandrel positioned on the distal curved geometry, where the mandrel decreases in outer diameter along and towards the distal tip positioned at the end of the distal curved geometry of the distal section of the guidewire. This arrangement may create (form) a compliant curved shape section, but is also configured to ensure that the distal tip deploys in a consistent spatial orientation each time (that is, each time the guidewire is deployed, or partially removed, from the accessory device such as a guidewire introducer). Given that a more proximal section of the guidewire is stiffer than the distal curved section, the distal curved section (also called a natural or biased curved section) is configured to adopt the interior shape of the accessory device once the distal curved section is received or positioned inside the accessory device since this is the lowest stress configuration for the distal curved section of the guidewire to adopt and force the orientation of the distal section to be the same shape. This results in a predictable, consistent deployment of the curved shape of the distal section of the guidewire.

For the case where the existing (known) medical guidewire assemblies include a piercing stylet device configured to puncture a biological wall of a patient, there may be unwanted or undesired physical contact between the piercing stylet device and the adjacently positioned tissue of the patient once (after) the piercing stylet device is deployed for initial puncturing of the biological wall. Once the biological wall has been initially punctured by the piercing stylet device, the piercing stylet device is no longer required for the purpose of puncturing (cutting, etc.) of the biological wall. It would be very desirable to shield or guard the piercing stylet device from further puncturing action after (once) the biological wall has been initially punctured by the piercing stylet device, and, in this manner, unwanted (inadvertent) puncturing (cutting) of the biological wall may be avoided. Therefore, it would be desirable to have a medical guidewire assembly include a piercing stylet device configured to initially puncture the biological wall and then to become disabled from further puncturing action, and unwanted or undesired physical contact between the piercing stylet device and the adjacently positioned tissue of the patient is prevented after the initial puncture of the biological wall. In this manner, safety to the patient may be improved (enhanced).

To mitigate, at least in part, at least one problem associated with the existing technology, there is provided (in accordance with a major aspect) an apparatus. The apparatus includes and is not limited to (comprises) a medical guidewire assembly including a flexible distal shaft section configured to be movable (be movable) through a guidewire introducer. The flexible distal shaft section is configured to have a predetermined spatial geometry once the flexible distal shaft section is moved beyond an exit portal, at least in part, from the guidewire introducer. The medical guidewire assembly also includes a piercing stylet device configured to puncture a biological wall of a patient in response to movement of the flexible distal shaft section through the guidewire introducer toward the biological wall (that is, once the flexible distal shaft section is moved through the guidewire introducer toward the biological wall). The predetermined spatial geometry, once formed, prevents (is configured to prevent), at least in part, physical contact between the piercing stylet device and the adjacently positioned tissue of the patient. In this manner, safety to the patient may be improved (enhanced).

To mitigate, at least in part, at least one problem associated with the existing technology, there is provided (in accordance with a major aspect) an apparatus. The apparatus includes and is not limited to (comprises) a medical guidewire assembly configured to be movable, at least in part, through an exit portal of a guidewire introducer. The exit portal is in fluid communication with an elongated interior channel extending, at least in part, longitudinally along the guidewire introducer. The exit portal is positionable proximate to a biological wall located within the body of a patient. The medical guidewire assembly has a flexible distal shaft section. The flexible distal shaft section is configured to extend (is extendable), at least in part, longitudinally along the elongated interior channel of the guidewire introducer once the flexible distal shaft section is received in, and supported by, the elongated interior channel (that is, the flexible distal shaft section is receivable in, and supported by, the elongated interior channel). The flexible distal shaft section is also configured to have a predetermined spatial geometry once the flexible distal shaft section is moved beyond an exit portal, at least in part, of, and unsupported by, the elongated interior channel of the guidewire introducer (that is, in response to removal, at least in part, of the flexible distal shaft section from the elongated interior channel of the guidewire introducer). The medical guidewire assembly also has a piercing stylet device extending from the flexible distal shaft section (from the end portion thereof). The piercing stylet device is configured to puncture the biological wall of the patient in response to (A) placement of the exit portal of the guidewire introducer (in use) proximate to the biological wall of the patient, and (B) movement of the flexible distal shaft section through the exit portal toward the biological wall. The predetermined spatial geometry (of the flexible distal shaft section) is configured to prevent, at least in part, physical contact between the piercing stylet device and the adjacently positioned tissue of the patient in response to formation of the predetermined spatial geometry by further movement of the flexible distal shaft section through the exit portal of the guidewire introducer after the biological wall is punctured by the piercing stylet device.

To mitigate, at least in part, at least one problem associated with the existing technology, there is provided (in accordance with a major aspect) a method. The method is for preventing, at least in part, physical contact between a piercing stylet device and the adjacently positioned tissue of a patient. The method includes and is not limited to (comprises) operation (A), operation (B), operation (C) and operation (D). Operation (A) includes moving, at least in part, a medical guidewire assembly through an exit portal of a guidewire introducer; the exit portal is in fluid communication with an elongated interior channel extending, at least in part, longitudinally along the guidewire introducer; the exit portal is positionable proximate to a biological wall located within the body of a patient, in which the medical guidewire assembly has a flexible distal shaft section. Operation (B) includes extending, at least in part, the flexible distal shaft section longitudinally along the elongated interior channel of the guidewire introducer once the flexible distal shaft section is received in, and supported by, the elongated interior channel (in which (i) the flexible distal shaft section is configured to have a predetermined spatial geometry once the flexible distal shaft section is moved beyond an exit portal, at least in part, of, and unsupported by, the elongated interior channel of the guidewire introducer, and (ii) the medical guidewire assembly also has a piercing stylet device extending from the flexible distal shaft section). Operation (C) includes puncturing the biological wall of the patient with the piercing stylet device in response to placement of the exit portal of the guidewire introducer (in use) proximate to the biological wall of the patient, and movement of the flexible distal shaft section through the exit portal toward the biological wall. Operation (D) includes permitting the predetermined spatial geometry of the flexible distal shaft section to prevent, at least in part, physical contact between the piercing stylet device and the adjacently positioned tissue of the patient in response to formation of the predetermined spatial geometry by further movement of the flexible distal shaft section through the exit portal of the guidewire introducer after the biological wall is punctured by the piercing stylet device.

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figures 1, 2:
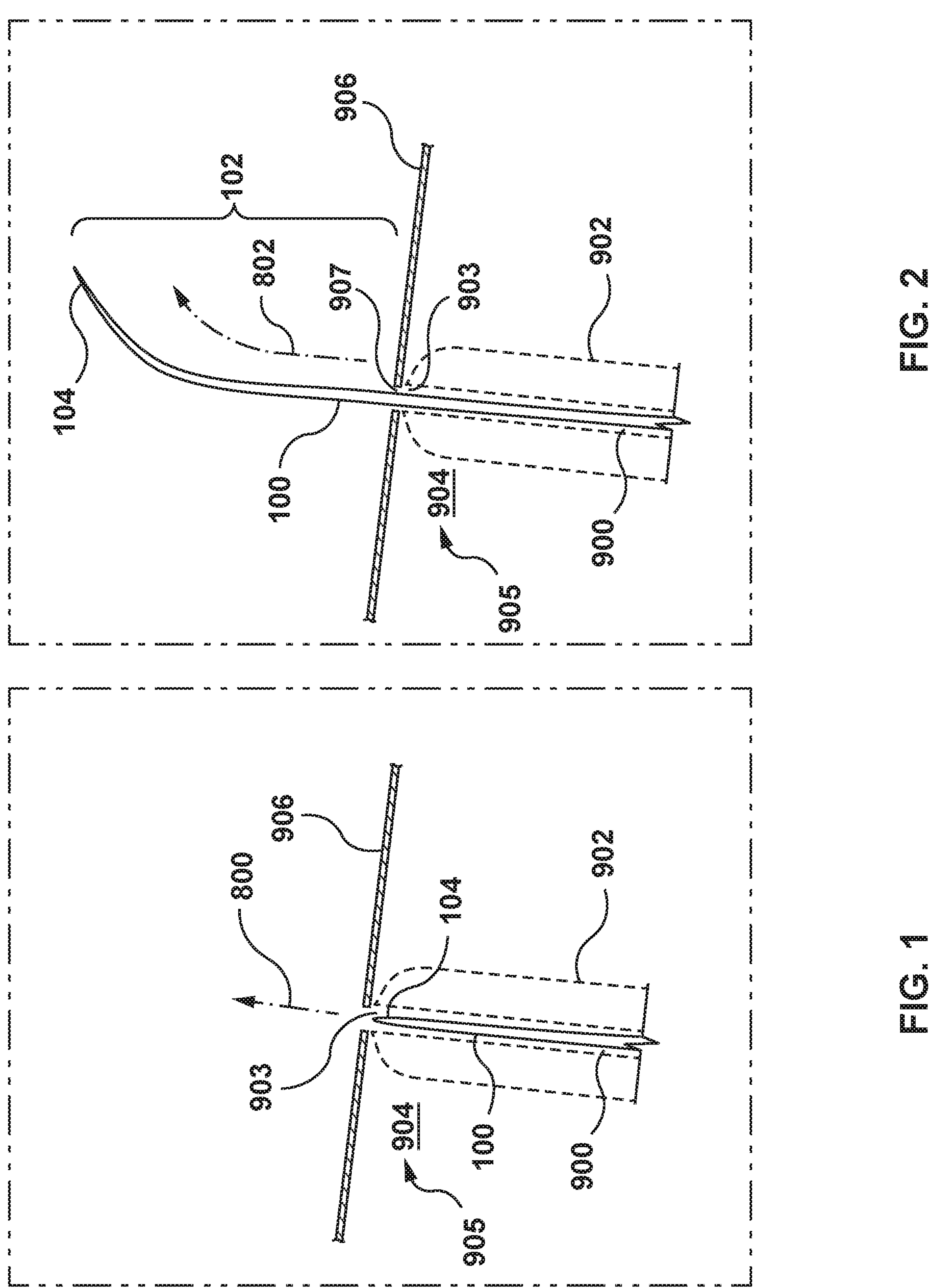
FIG. 1, FIG. 2, FIG. 3 and FIG. 4 (SHEET 1 of 5 SHEETS) depict side views of embodiments of a medical guidewire assembly.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not depicted to provide a less obstructed view of the embodiments of the present disclosure.

| LISTING OF REFERENCE NUMERALS USED IN THE DRAWINGS | |
|---|---|
| medical guidewire assembly 100 | flexible distal shaft section 102 |
| spatial geometry 103 | stylet device 104 |
| shaft guard portion 106 | distal straight section 108 |
| outer diameter 110 | shielding direction 112 |
| articulation points 114 | rigid spaced-apart members 116 |
| direction 800 | direction 802 |
| direction 803 | direction 804 |
| lines 806 | interior channel 900 |
| guidewire introducer 902 | exit portal 903 |
| body 904 | patient 905 |
| biological wall 906 | puncture hole 907 |

DETAILED DESCRIPTION OF THE NON-LIMITING EMBODIMENT(S)

The following detailed description is merely exemplary and is not intended to limit the described embodiments or the application and uses of the described embodiments. As used, the word “exemplary” or “illustrative” means “serving as an example, instance, or illustration.” Any implementation described as “exemplary” or “illustrative” is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the claim is defined by the claims (in which the claims may be amended during patent examination after the filing of this application). For the description, the terms “upper,” “lower,” “left,” “rear,” “right,” “front,” “vertical,” “horizontal,” and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase “at least one” is equivalent to “a”. The aspects (examples, alterations, modifications, options, variations, embodiments and any equivalent thereof) are described regarding the drawings. It should be understood that the invention is limited to the subject matter provided by the claims, and that the invention is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, “configured to” may include the meaning “either directly or indirectly” unless specifically stated otherwise.

FIG. 1, FIG. 2, FIG. 3 and FIG. 4 depict side views of embodiments of a medical guidewire assembly 100.

Referring to the embodiment as depicted in FIG. 1, an apparatus (in accordance with a less specific embodiment) includes and is not limited to (comprises) a medical guidewire assembly 100. The medical guidewire assembly 100 includes and is not limited to a flexible distal shaft section 102 that is movable through (an elongated length of) a guidewire introducer 902. Embodiments of the guidewire introducer 902 may include a catheter, a dilator, etc., and any equivalent thereof. The guidewire introducer 902 is configured to introduce the medical guidewire assembly 100 into the body 904 of a patient 905. In medicine, a guidewire introducer 902 is a tube made from medical grade materials serving a broad range of functions. The guidewire introducer 902 is a medical device that can be inserted into the body (of the patient 905) for the treatment of a variety of diseases or the performance of a variety of procedures. By modifying the material or adjusting the way the guidewire introducer 902 is manufactured, it may be possible to tailor the guidewire introducer 902 for cardiovascular, urological, gastrointestinal, neurovascular, and ophthalmic applications, etc., and any equivalent thereof.

In accordance with the embodiment as depicted in FIG. 1, the medical guidewire assembly 100 or the flexible distal shaft section 102 may include a stainless steel alloy. The stainless steel alloy is sufficiently stiff that a physician may find the guidewire to be preferable for exchanging catheters across the septum while the outer diameter of the guidewire may enable compatibility with a majority of transseptal catheters and systems, etc. The medical guidewire assembly 100 or the flexible distal shaft section 102 may have a diameter of about 0.032 inches (preferably, this is the maximum diameter, at its thickest section).

In accordance with the embodiment as depicted in FIG. 1, the medical guidewire assembly 100 or the flexible distal shaft section 102 may include any type of biologically compatible material, such as any stainless steel material or alloy.

In accordance with the embodiment as depicted in FIG. 1, an equivalent to the medical guidewire assembly 100 may include a rigid cannula (or a flexible cannula) with a piercing stylet device 104 positioned inside of the cannula, in which the piercing stylet device 104 is configured to be retracted through the cannula once the piercing stylet device 104 has pierced through the biological wall 906 in order to mitigate any further risk of physical contact with the tissue of the patient 905.

In accordance with the embodiment, the medical guidewire assembly 100 may include any guidewire and any equivalent thereof that is able to (configured to) mechanically pierce the biological wall 906, and after which the flexible distal shaft section 102 articulates to form the predetermined spatial geometry 103 (the requisite curved geometry) once the flexible distal shaft section 102 is removed from the interior (the elongated interior channel 900) of the guidewire introducer 902. Further, any material that may change shape under mechanical, electrical, thermal, magnetic, or acoustic exposure may be used in the medical guidewire assembly 100. The flexible distal shaft section 102 is configured to articulate to form the predetermined spatial geometry 103 once the flexible distal shaft section 102 is removed from the interior (the elongated interior channel 900) of the guidewire introducer 902.

Figures 3, 4:
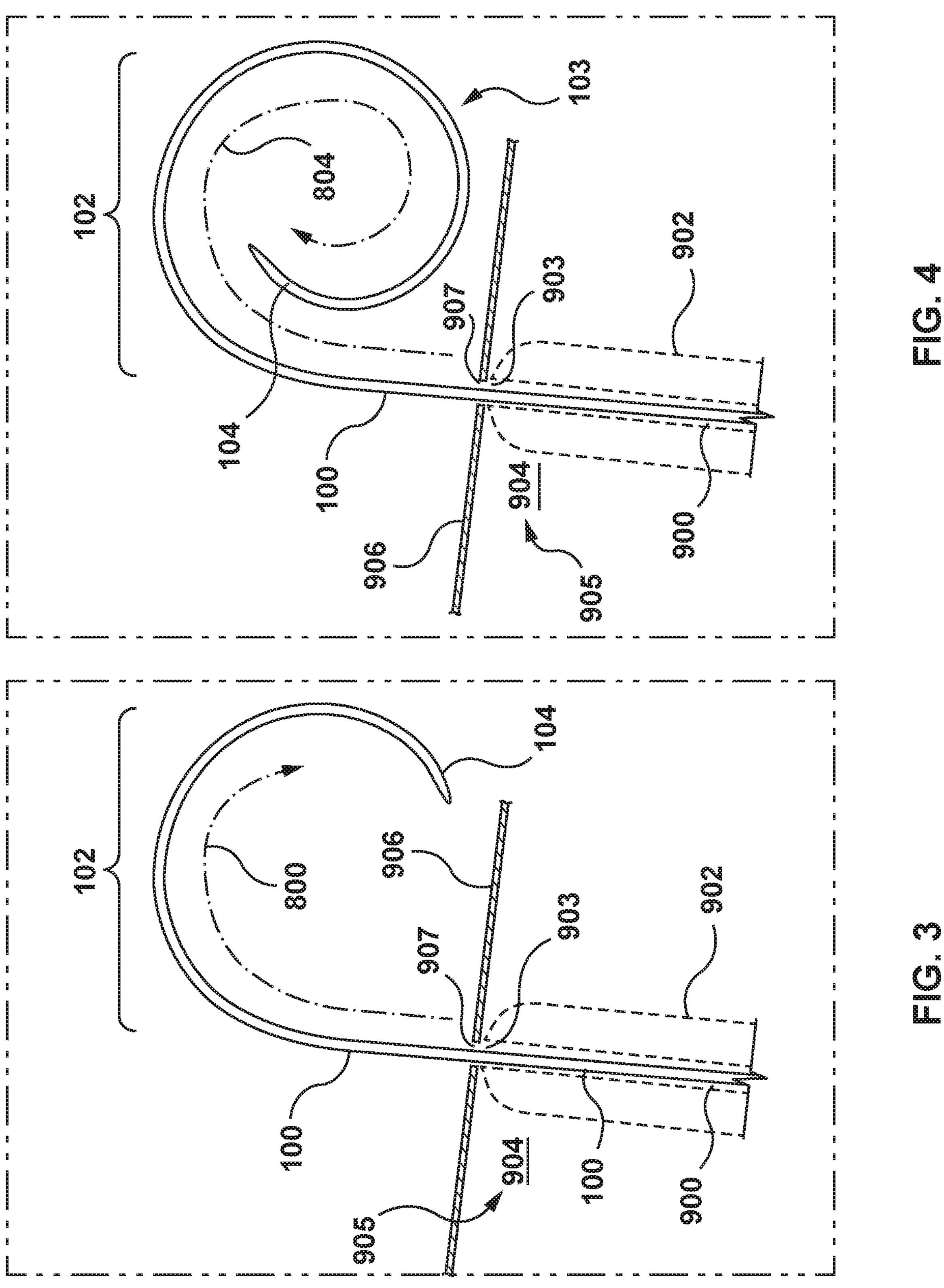

Referring to the embodiment as depicted in FIG. 1, the flexible distal shaft section 102 is configured to have a predetermined spatial geometry 103 once the flexible distal shaft section 102 is removed, at least in part, from the guidewire introducer 902. The predetermined spatial geometry 103 is a geometry (shape) of the flexible distal shaft section 102 that is formed once (or repeatably formed every time) the flexible distal shaft section 102 is removed (at least in part) from the interior (elongated interior channel 900) of the guidewire introducer 902 (as depicted, for instance, in the embodiment of FIG. 4). The flexible distal shaft section 102 has a flexible bias (natural or inherent flexible tendency) to become formed into the predetermined spatial geometry 103 once the flexible distal shaft section 102 is removed (at least in part) from the interior (elongated interior channel 900) of the guidewire introducer 902. It will be appreciated that once the flexible distal shaft section 102 is inserted (at least in part) into the interior (elongated interior channel 900) of the guidewire introducer 902, the predetermined spatial geometry 103 (as depicted in the embodiment of FIG. 4) collapses into the shape (as depicted in the embodiment of FIG. 1).

Referring to the embodiment as depicted in FIG. 1, the guidewire introducer 902 also includes a piercing stylet device 104.

Referring to the embodiment as depicted in FIG. 1, the piercing stylet device 104 is configured to puncture a biological wall 906 of a patient 905; this is done in response to movement (along a direction 800) of the flexible distal shaft section 102 through the guidewire introducer 902 toward the biological wall 906 (as depicted in the embodiment of FIG. 1).

Referring to the embodiment as depicted in FIG. 2, the piercing stylet device 104 was moved, and (as a result) the piercing stylet device 104 punctured (cut) the biological wall 906 of the patient 905 thereby forming a puncture hole 907 through the biological wall 906 (as a result); this is done once (after) the flexible distal shaft section 102 was moved (at least in part) through the guidewire introducer 902 toward (and then through) the biological wall 906. As the flexible distal shaft section 102 is made to continue movement (along a direction 802), the flexible distal shaft section 102 changes its shape (orientation) to become, for instance, curved, etc. This condition is a result of the flexible biasing built into the flexible distal shaft section 102.

In accordance with the embodiment as depicted in FIG. 2, the flexible distal shaft section 102 includes a distal end section with a piercing stylet device 104 extending therefrom. The piercing stylet device 104 is configured to puncture (capable of puncturing) through the biological wall 906. The amount of force used to puncture the tissue (wall) may be achieved via a bevel that makes it possible to relatively easily pierce through (puncture or cut) the biological wall 906.

In accordance with the embodiment as depicted in FIG. 2, the piercing stylet device 104 is configured to mechanically puncture a biological wall (such as, the inter-atrial septum of the heart). The piercing stylet device 104 is configured to pierce the biological wall 906 (the septum) when or once the piercing stylet device 104 is advanced (moved) through the guidewire introducer 902 (or any equivalent, such as an accessory medical device).

In accordance with the embodiment as depicted in FIG. 2, any degree of sharpness may be acceptable for the piercing stylet device 104 (distal tip profile). It will be appreciated that certain distal tip profiles may reduce the required force to create a puncture through the biological wall 906; there may exist a level of applied force at which any type of the stylet device 104 may puncture through the biological wall 906. The stylet device 104 may include a blunt end portion that may still mechanically puncture the biological wall 906 as long as sufficient force is applied to the medical guidewire assembly 100.

In accordance with the embodiment as depicted in FIG. 2, the piercing stylet device 104 (sharp distal tip) may have any suitable profile. The degree of sharpness of the piercing stylet device 104 reduces, at least in part, the force with which the piercing stylet device 104 may mechanically cross (pass through) the biological wall 906 (such as the inter-atrial septum of the heart).

In accordance with the embodiment as depicted in FIG. 3, the piercing stylet device 104 is further moved through the puncture hole 907 formed through the biological wall 906 of the patient 905 as a result of further movement of the flexible distal shaft section 102 through the guidewire introducer 902 toward the biological wall 906. As the flexible distal shaft section 102 is made to continue movement (along a direction 803), the flexible distal shaft section 102 continues to change its shape (orientation) to become, for instance, more curved, etc. This is a further result of the flexible biasing built into the flexible distal shaft section 102.

In accordance with the embodiment as depicted in FIG. 4, the piercing stylet device 104 is, once again, further moved through the puncture hole 907 formed through the biological wall 906 of the patient 905 as a result of further movement of the flexible distal shaft section 102 through the guidewire introducer 902 toward the biological wall 906. The predetermined spatial geometry 103, once formed, prevents, at least in part, physical contact between the piercing stylet device 104 and the adjacently positioned tissue of the patient 905. The predetermined spatial geometry 103 maintains the piercing stylet device 104 and the adjacently positioned tissue of the patient 905 in a non-contact relationship with each other, and once the predetermined spatial geometry 103 becomes formed, the predetermined spatial geometry 103 prevents, at least in part, physical contact between the piercing stylet device 104 and the adjacently positioned tissue of the patient 905 (the piercing stylet device 104 and the adjacently positioned tissue of the patient 905 are maintained in a spaced-apart relationship). Once the flexible distal shaft section 102 is further made to continue movement (along a direction 804) and become (fully) extended, the flexible distal shaft section 102 continues to change its shape (orientation) to become, for instance, even more curved, etc. This is a further result of the flexible biasing built into the flexible distal shaft section 102.

In accordance with the embodiment as depicted in FIG. 4, the predetermined spatial geometry 103 may include a distal curved section. The predetermined spatial geometry 103 is mounted to the base of the piercing stylet device 104; the piercing stylet device 104 is mounted to the end of the predetermined spatial geometry 103. The predetermined spatial geometry 103, preferably, wraps around itself in a spiral configuration once the flexible distal shaft section 102 is fully relaxed as depicted in FIG. 4 (that is, when the flexible distal shaft section 102 is removed, at least in part, from the guidewire introducer 902, and the flexible distal shaft section 102 becomes unsupported by the guidewire introducer 902); for instance, this is done, preferably, so there is no linear displacement vector that can approach along the plane of the predetermined spatial geometry 103 that may contact the piercing stylet device 104 without the linear displacement vector first contacting another section of the predetermined spatial geometry 103.

In accordance with the embodiment as depicted in FIG. 4, when the piercing stylet device 104 is positioned fully inside the left atrium (of the patient 905) and the flexible distal shaft section 102 is in a relaxed configuration (curved or non-linear condition or shape), the predetermined spatial geometry 103 (such as a shaped curve) of the flexible distal shaft section 102 forms and prevents physical contact between the piercing stylet device 104 (the sharp distal tip) and any adjacently positioned tissue. For instance, when examined on the plane of the curvature of the predetermined spatial geometry 103, the piercing stylet device 104 may be moved in any direction without the piercing stylet device 104 being able to contact any adjacently located tissue of the patient 905. This configuration prevents, at least in part, inadvertent tissue damage by avoiding physical contact between the piercing stylet device 104 and the adjacently located tissue of the patient 905.

In accordance with the embodiment as depicted in FIG. 4, the predetermined spatial geometry 103 (also called a protective geometry) is configured to enclose (guard) the piercing stylet device 104, and prevent the piercing stylet device 104 from physically contacting any adjacently located tissue of the patient 905 once (or when) the predetermined spatial geometry 103 is positioned (placed or located) in a relaxed shape outside of the guidewire introducer 902.

In accordance with the embodiment as depicted in FIG. 4, the predetermined spatial geometry 103 is configured to prevent physical contact between the piercing stylet device 104 and the adjacently located tissue of the patient 905, thereby preventing, at least in part, inadvertent trauma of the tissue after the piercing stylet device 104 is made to pass through the biological wall 906.

In accordance with the embodiment as depicted in FIG. 4, the predetermined spatial geometry 103 (the shaped section or the curved geometry) may include a circular spiral of material (such as a stainless-steel material) with a continually changing radius where the outer diameter tapers down (preferably constantly) from a maximum outer diameter at the start of the curve to a minimal outer diameter (such as, about a 0.006 inch minimal outer diameter), and then finishes with a sharpened bevel positioned at the distal tip of the flexible distal shaft section 102. This arrangement, preferably, creates (forms) a curve that is compliant and atraumatic to tissue, and/or is sufficiently stiff enough to maintain left atrial access (that is, access through the biological wall 906) once the flexible distal shaft section 102 is in its relaxed configuration (as depicted in FIG. 4, for example). Further, this arrangement may result in a consistent and predictable deployment orientation of the piercing stylet device 104 positioned at the distal tip of the flexible distal shaft section 102. With quick reference to FIG. 1, the stiffer proximal sections of the predetermined spatial geometry 103 (curved section) adopt the configuration of the interior shape of elongated interior channel 900 of the guidewire introducer 902 (also called the accessory device), and force more distal sections of the flexible distal shaft section 102 to adopt the same configuration of the interior shape of the guidewire introducer 902.

In accordance with the embodiment as depicted in FIG. 4, the overall size of the predetermined spatial geometry 103 (the curve), preferably, may be able to fit in the left atrium of the heart, but may also be large enough to inhibit the medical guidewire assembly 100 from being easily pulled out (of the heart). Given this requirement, it may be appropriate for a distal curve size to range from about 24.0 millimeters (mm) to about 50.0 millimeters (mm).

In accordance with the embodiment as depicted in FIG. 4, the predetermined spatial geometry 103 (circular spiral with changing radius) may be such that the piercing stylet device 104 exists (or is positioned) within the confines of the predetermined spatial geometry 103 (that is, within the innermost rotation of the curve) and is surrounded by the predetermined spatial geometry 103 (the curved material) on all sides (such as, when viewed on the plane of the predetermined spatial geometry 103).

In accordance with the embodiment as depicted in FIG. 4, any material that is compliant enough to be manually straightened and then springs back (when released) to form the predetermined spatial geometry 103 (a distal curved geometry) may be sufficient. Preferably, the spiral or loop does not need to have smooth continuous edges but may come to represent any geometric shape such as a square, a rectangle, or a triangle (to list a few embodiments).

In accordance with the embodiment as depicted in FIG. 4, non-compliant materials may also be used in the predetermined spatial geometry 103. For instance, a stiff material with points of articulation that are able to straighten the flexible distal shaft section 102 for puncturing the biological wall 906 (such as the inter-atrial septum) and then be formed into the predetermined spatial geometry 103 (such as a general curved shape) may be utilized. It will be appreciated that any material that is able to change shape or bend under mechanical, electrical, thermal, magnetic, or acoustic exposure to form the predetermined spatial geometry 103 (with a requisite curved shape) may be used.

In accordance with the embodiment as depicted in FIG. 4, the predetermined spatial geometry 103 (the curved geometry) is configured (arranged) as a straight line that cannot be drawn to the piercing stylet device 104 (distal tip) without first contacting another portion of the predetermined spatial geometry 103 of the flexible distal shaft section 102.

In accordance with the embodiment as depicted in FIG. 4, the predetermined spatial geometry 103 (the curved geometry) forms a closed loop arrangement configured to prevent (at least in part) a straight line from being drawn to the piercing stylet device 104 without first contacting another portion of the spatial geometry 103.

In accordance with the embodiment as depicted in FIG. 4, the flexible distal shaft section 102 is movable through a guidewire introducer 902. The flexible distal shaft section 102 is configured to have a predetermined spatial geometry 103 once the flexible distal shaft section 102 is removed, at least in part, from the elongated interior channel 900 of the guidewire introducer 902. The predetermined spatial geometry 103, once formed, prevents, at least in part, physical contact between the piercing stylet device 104 and the adjacently positioned tissue of the patient 905.

In accordance with the embodiment as depicted in FIG. 4, the medical guidewire assembly 100, the flexible distal shaft section 102 and the piercing stylet device 104 are each configured to be inserted into a confined space defined by the patient 905. The guidewire introducer 902 is (preferably) configured to guide the insertion of the medical guidewire assembly 100 with the flexible distal shaft section 102 into the confined space defined by the patient 905 (after the guidewire introducer 902 is installed in the patient 905). The flexible distal shaft section 102 includes (preferably) a relatively thin and flexible wire (an elongated flexible shaft) configured to be inserted into a confined or tortuous space (such as the confined space defined within the patient 905). The flexible distal shaft section 102 includes, preferably, a flexible tube (made from a medical grade material). The flexible distal shaft section 102 includes is (preferably) impermeable by a bodily fluid located in the confined space defined by the patient 905. The flexible distal shaft section 102 includes, preferably, SAE (Society of Automotive Engineering) Type 304 Stainless Steel. SAE Type 304 stainless steel contains both chromium (from between 15% to 20%) and nickel (between 2% to 10.5%) metals as the main non-iron constituents. The flexible distal shaft section 102 includes (in accordance with another option) superelastic nitinol. Nitinol alloys exhibit two closely related and unique properties: shape memory effect (SME) and superelasticity (SE; also called pseudo elasticity or PE). Shape memory is the ability of nitinol to undergo deformation at one temperature, then recover its original, undeformed shape upon heating above its transformation temperature. Superelasticity occurs at a narrow temperature range just above its transformation temperature; in this case, no heating is necessary to cause the undeformed shape to recover, and the material exhibits enormous elasticity, from about ten (10) to thirty (30) times that of ordinary metal. The flexible distal shaft section 102 includes (in accordance with another option) bio-compatible materials properties suitable for sufficient performance properties (dielectric strength, thermal performance, insulation and corrosion, water and heat resistance) for safe performance to comply with industrial and regulatory safety standards (or compatible for medical usage). Reference is made to the following publication for consideration in the selection of a suitable material: Plastics in Medical Devices: Properties, Requirements, and Applications; 2nd Edition; author: Vinny R. Sastri; hardcover ISBN: 9781455732012; published: 21 Nov. 2013; publisher: Amsterdam [Pays-Bas]: Elsevier/William Andrew, [2014].

Referring to the embodiment as depicted in FIG. 1, an apparatus (in accordance with a more specific embodiment) includes and is not limited to a medical guidewire assembly 100 configured to be movable, at least in part, through an exit portal 903 of the guidewire introducer 902. The exit portal 903 is in fluid communication with an elongated interior channel 900 extending (at least in part) longitudinally along a guidewire introducer 902. The exit portal 903 is positionable proximate to a biological wall 906 located within the body 904 of a patient 905 (such as, the inter-atrial septum of the heart of the patient 905). The medical guidewire assembly 100 has a flexible distal shaft section 102.

In accordance with the embodiment as depicted in FIG. 1, the flexible distal shaft section 102 is positioned within the medical guidewire assembly 100 (and then, preferably, the exit portal 903 is positioned proximate to the biological wall 906).

Referring to the embodiments as depicted in FIG. 2, FIG. 3 and FIG. 4, the flexible distal shaft section 102 is configured to extend (at least in part), or is extendable, longitudinally along the elongated interior channel 900 of the guidewire introducer 902 once the flexible distal shaft section 102 is received in, and supported by, the elongated interior channel 900.

In accordance with the embodiment as depicted in FIG. 4, the flexible distal shaft section 102 is also configured to have a predetermined spatial geometry 103 (such as a curved shape) once the flexible distal shaft section 102 is removed from, and becomes unsupported by, the elongated interior channel 900 of the guidewire introducer 902.

Briefly referring back to the embodiment as depicted in FIG. 1, the medical guidewire assembly 100 also has a piercing stylet device 104 extending from the flexible distal shaft section 102.

Briefly referring back to the embodiment as depicted in FIG. 2, the piercing stylet device 104 is configured to (mechanically) puncture (cut) the biological wall 906 of the patient 905 (thereby forming the puncture hole 907 through the biological wall 906); this is done in response to placement of the exit portal 903 of the guidewire introducer 902 (in use) proximate to the biological wall 906 of the patient 905, and then movement of the flexible distal shaft section 102 through the exit portal 903 toward the biological wall 906.

In accordance with the embodiment as depicted in FIG. 4, the predetermined spatial geometry 103 of the flexible distal shaft section 102 is configured to prevent, at least in part, physical contact between the piercing stylet device 104 and the adjacently positioned (adjacently located) tissue of the patient 905; this is done in response to formation of the predetermined spatial geometry 103 by further movement (along the direction 800 as depicted in FIG. 1) of the flexible distal shaft section 102 through the exit portal 903 of the guidewire introducer 902 after the biological wall 906 is punctured (as depicted in FIG. 2) by the piercing stylet device 104. The predetermined spatial geometry 103 assists in prevention of the piercing stylet device 104 from potentially inflicting further or unwanted tissue damage after the piercing stylet device 104 punctures (as depicted in FIG. 2) the biological wall 906 once the flexible distal shaft section 102 is further advanced through the exit portal 903 of the guidewire introducer 902 along the direction 800 (as depicted in FIG. 1).

Referring to the embodiments as depicted in FIG. 1 to FIG. 4, there is provided (and depicted) a method of preventing, at least in part, physical contact between a piercing stylet device 104 and the adjacently positioned tissue of a patient 905. The method includes (comprises) various operations (as described below).

Referring to the embodiment as depicted in FIG. 1, operation (A) includes positioning an exit portal 903 of the guidewire introducer 902 (in use) proximate to a biological wall 906 located within the body 904 of a patient 905.

Referring to the embodiment as depicted in FIG. 1, operation (B) includes moving, at least in part, a medical guidewire assembly 100 through the exit portal 903 of the guidewire introducer 902 (the exit portal 903 is in fluid communication with an elongated interior channel 900 extending, at least in part, longitudinally along the guidewire introducer 902, in which the medical guidewire assembly 100 has a flexible distal shaft section 102).

Referring to the embodiment as depicted in FIG. 1, operation (C) includes extending, at least in part, the flexible distal shaft section 102 longitudinally along the elongated interior channel 900 of the guidewire introducer 902 toward the biological wall 906 (that is, after or once the flexible distal shaft section 102 is received in, and supported by, the elongated interior channel 900); the flexible distal shaft section 102 is configured to have a predetermined spatial geometry 103 once (after) the flexible distal shaft section 102 is removed, at least in part, from, and is unsupported by, the elongated interior channel 900 of the guidewire introducer 902 (and in which the medical guidewire assembly 100 also has a piercing stylet device 104 extending from the flexible distal shaft section 102).

Referring to the embodiment as depicted in FIG. 2, operation (D) includes puncturing the biological wall 906 of the patient 905 with the piercing stylet device 104; this is done in response to placement of the exit portal 903 of the guidewire introducer 902 (in use) proximate to the biological wall 906 of the patient 905, and movement of the flexible distal shaft section 102 through the exit portal 903 toward the biological wall 906.

Referring to the embodiment as depicted in FIG. 4, operation (E) includes permitting the predetermined spatial geometry 103 of the flexible distal shaft section 102 to prevent, at least in part, physical contact between the piercing stylet device 104 and the adjacently positioned tissue of the patient 905 in response to formation of the predetermined spatial geometry 103 by further movement of the flexible distal shaft section 102 through the exit portal 903 of the guidewire introducer 902 after the biological wall 906 is punctured by the piercing stylet device 104.

In accordance with the embodiment as depicted in FIG. 4, the flexible distal shaft section 102 is configured to become fully relaxed and unsupported by the elongated interior channel 900 of the guidewire introducer 902 in response to removal of the flexible distal shaft section 102, via the exit portal 903, from the elongated interior channel 900. The flexible distal shaft section 102 is configured to become fully relaxed and unsupported by the elongated interior channel 900 of the guidewire introducer 902 in response to progress of the flexible distal shaft section 102 beyond the exit portal 903, from the elongated interior channel 900.

Figure 5:
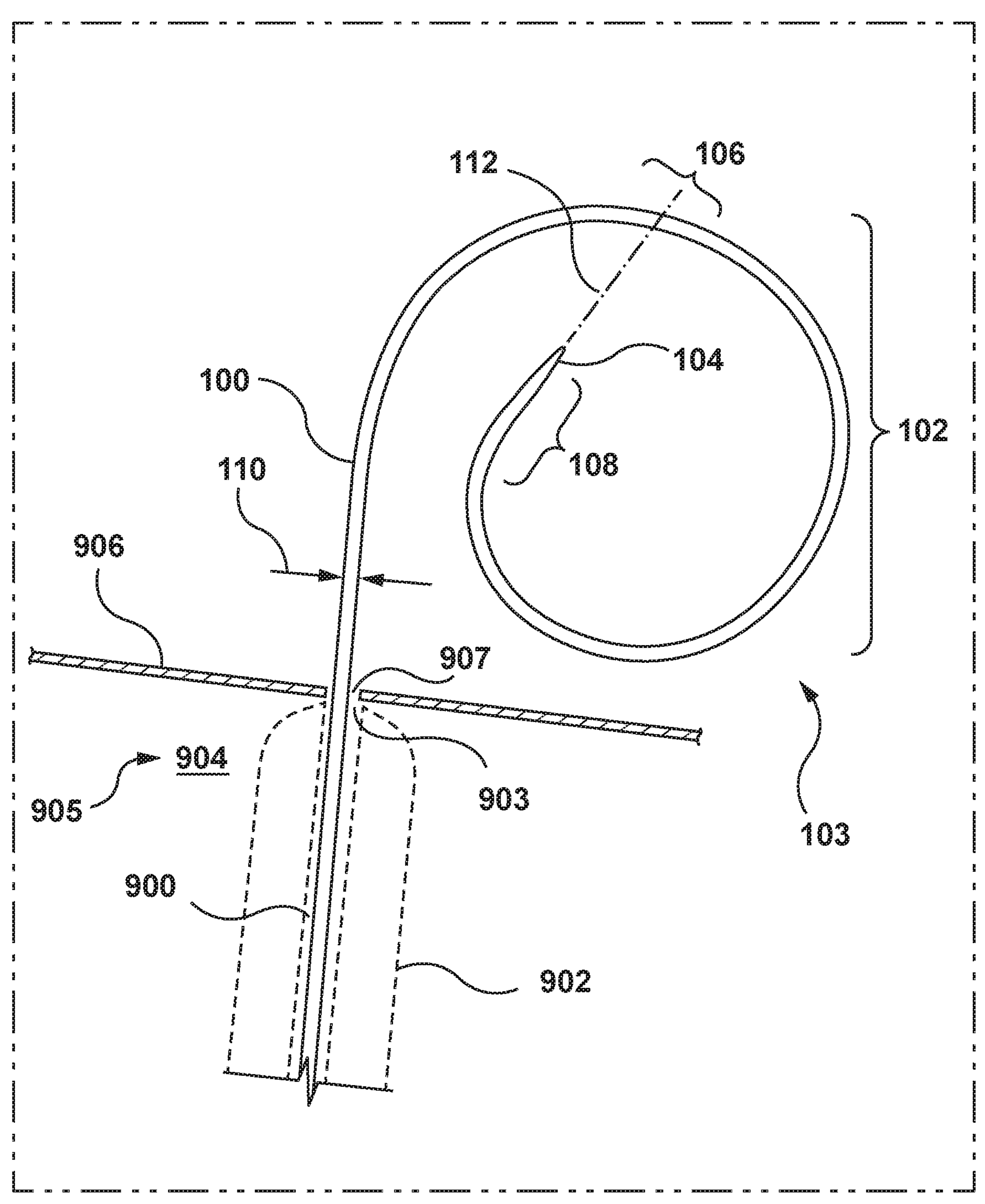
FIG. 5 and FIG. 6 (SHEET 2 and 3 of 5 SHEETS) depict close-up side views of embodiments of the medical guidewire assembly of FIG. 4.
Figure 6:
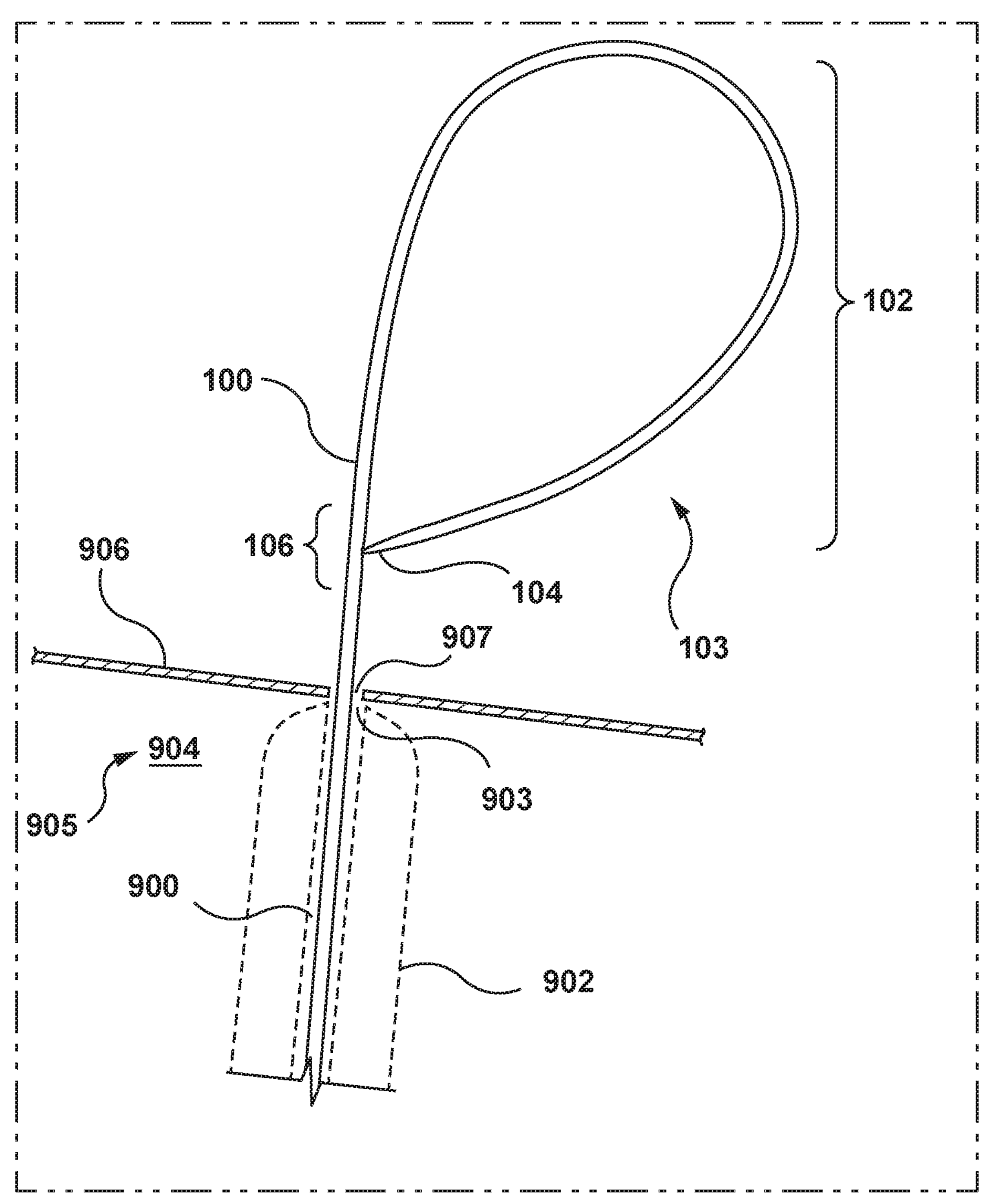

FIG. 5 and FIG. 6 depict close-up side views of embodiments of the medical guidewire assembly 100 of FIG. 4.

In accordance with the embodiment as depicted in FIG. 5, the predetermined spatial geometry 103 is configured to form a spiral configuration in response to removal of the flexible distal shaft section 102, via the exit portal 903, from the elongated interior channel 900. Preferably, there is no linear displacement vector on the plane of the curvature that can contact the distal tip without also contacting another section of the piercing stylet.

Referring to the embodiments as depicted in FIG. 5 and FIG. 6, the flexible distal shaft section 102 includes a shaft guard portion 106 spaced apart from the piercing stylet device 104. The shaft guard portion 106 is configured to face and shield the piercing stylet device 104 in response to formation of the predetermined spatial geometry 103 by further movement of the flexible distal shaft section 102 through the exit portal 903 of the guidewire introducer 902 after the biological wall 906 is punctured by the piercing stylet device 104; this is done in such a way that the shaft guard portion 106, in use, prevents contact between the piercing stylet device 104 and the adjacently positioned tissue of the patient 905. For instance, the shaft guard portion 106 faces the piercing stylet device 104 along a shielding direction 112.

In accordance with the embodiments as depicted in FIG. 5 and FIG. 6, the predetermined spatial geometry 103 is configured to be biased to lie on, and extend along, a single planar surface in response to removal of the flexible distal shaft section 102, via the exit portal 903, from the elongated interior channel 900. There is no linear displacement vector on the plane of the curvature that can contact the distal tip without also contacting another section of the piercing stylet.

In accordance with the embodiment as depicted in FIG. 5, the piercing stylet device 104 is positioned outside of (and is no longer guarded by) the elongated interior channel 900 of the guidewire introducer 902. Once positioned, or moved, out from the elongated interior channel 900, the predetermined spatial geometry 103 is formed (as depicted as a spiral curved geometry). The spiral curved geometry is depicted with an increasing radius from the piercing stylet device 104. The predetermined spatial geometry 103 is depicted in a relaxed configuration (which occurs once the flexible distal shaft section 102 is removed from the elongated interior channel 900 of the guidewire introducer 902). For this embodiment, the piercing stylet device 104 is positioned inside the spiral formation (shaped formation), and in this manner, the piercing stylet device 104 remains in a non-contact relationship with the adjacently positioned tissue of the patient 905 (that is, there is no physical contact between the piercing stylet device 104 and the adjacently positioned tissue of the patient 905 once the predetermined spatial geometry 103 is deployed in a formed state as depicted in the embodiment of FIG. 5). The outer diameter of the predetermined spatial geometry 103 decreases in size (tapers) toward the location of the piercing stylet device 104. This arrangement ensures, at least in part, a relatively more consistent deployment orientation of the flexible distal shaft section 102 from the guidewire introducer 902 (as stiffer proximal sections adopt the curvature of the guidewire introducer 902 and force the same orientation of less stiff distal sections of the flexible distal shaft section 102).

In accordance with the embodiment as depicted in FIG. 5, the outer diameter 110 of the predetermined spatial geometry 103 may be any size that may fit within the patient.

In accordance with the embodiment as depicted in FIG. 5, the flexible distal shaft section 102 includes, preferably, an outer diameter tapering down at the distal end of the flexible distal shaft section 102.

In accordance with the embodiment as depicted in FIG. 5, the predetermined spatial geometry 103 of the flexible distal shaft section 102 includes, preferably, a circular spiral curve (that is, after the piercing stylet device 104 punctures the biological wall 906 and then moves out from the guidewire introducer 902 and through the biological wall 906). However, it will be appreciated that the predetermined spatial geometry 103 may be (may include) any suitable shape. Preferably, the predetermined spatial geometry 103 forms a shape that makes it relatively difficult, if not outright impossible, to permit physical contact between the piercing stylet device 104 and the adjacently positioned tissue (that is, after the piercing stylet device 104 punctures the biological wall 906 and then moves out from the guidewire introducer 902 and through the biological wall 906).

In accordance with the embodiment as depicted in FIG. 5, the piercing stylet device 104 has a pointed bevel. The piercing stylet device 104 is configured to (is capable of) puncturing through the biological wall 906. Proximal to the piercing stylet device 104, there is located a distal straight section 108 (of the flexible distal shaft section 102). For instance, the distal straight section 108 may have a length from between about 4.0 millimeters (mm) and about 10.0 millimeters (mm) in length to facilitate a straight trajectory of the piercing stylet device 104 through the desired puncture site (such as the puncture hole 907) formed in or through the biological wall 906 (such as the septum of the heart).

In accordance with the embodiment as depicted in FIG. 6, the predetermined spatial geometry 103 forms a closed loop (that is, after the piercing stylet device 104 punctures the biological wall 906 and then moves out from the guidewire introducer 902 and through the biological wall 906).

In accordance with the embodiment as depicted in FIG. 6, the piercing stylet device 104 and the predetermined spatial geometry 103 cooperate to form a closed-loop geometry once the predetermined spatial geometry 103 is placed in its relaxed configuration (that is, once the flexible distal shaft section 102 is removed from the elongated interior channel 900 of the guidewire introducer 902). In this embodiment, the piercing stylet device 104 makes physical contact (or is in a close proximal position) with a shaft guard portion 106 (a portion) of the flexible distal shaft section 102, and (as a result) the piercing stylet device 104 is not able to physically contact the adjacently positioned tissue of the patient 905.

Referring to the embodiment as depicted in FIG. 6, the predetermined spatial geometry 103 is placed in a relaxed configuration, and the predetermined spatial geometry 103 wraps around (itself, at least in part) in such a way that the piercing stylet device 104 may physically contact a portion of the flexible distal shaft section 102 (or the body of the medical guidewire assembly 100); in this manner, the piercing stylet device 104 and the predetermined spatial geometry 103 of the flexible distal shaft section 102 cooperate to form a closed loop shape.

Figures 7, 8, 9:
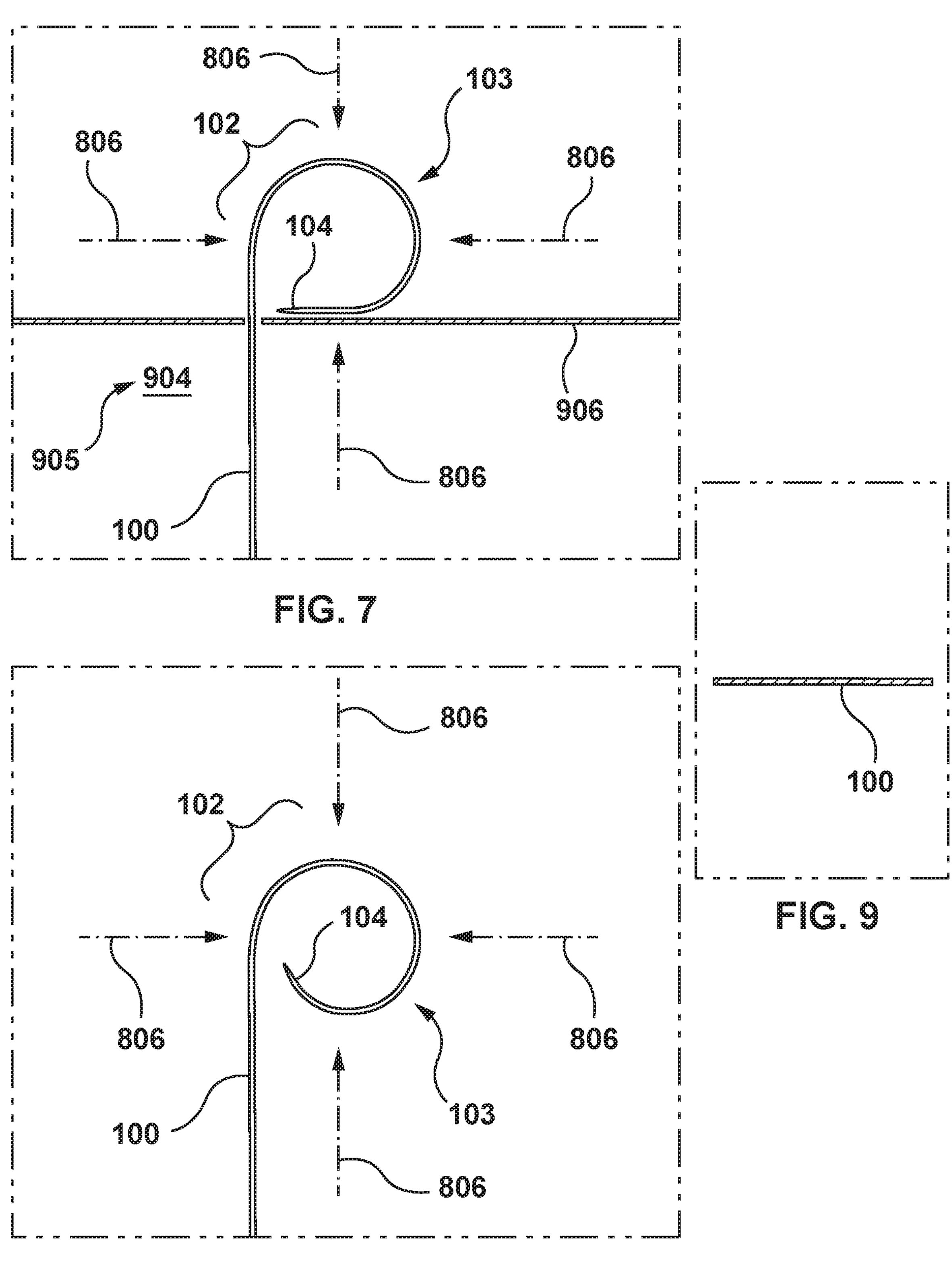
FIG. 7 and FIG. 8 (SHEET 4 of 5 SHEETS) depict side views of embodiments of the medical guidewire assembly of FIG. 4.
FIG. 9 (SHEET 4 of 5 SHEETS) depicts a top view of an embodiment of the medical guidewire assembly of FIG. 7 (or FIG. 8)

FIG. 7 and FIG. 8 depict side views of embodiments of the medical guidewire assembly 100 of FIG. 4.

Referring to the embodiment as depicted in FIG. 7, the flexible distal shaft section 102 is positioned in a relaxed configuration (that is, once the flexible distal shaft section 102 has been removed from the elongated interior channel 900 of the guidewire introducer 902 that is depicted in FIG. 4). In the relaxed configuration, the flexible distal shaft section 102 forms (is configured to form) the predetermined spatial geometry 103 (for guarding of the piercing stylet device 104 thereby preventing unwanted puncturing of the adjacently located tissue, such as the biological wall 906). The dashed lines 806 depict vectors (directions of relative movement of tissue) travelling from outside of the predetermined spatial geometry 103 inwards to the predetermined spatial geometry 103, similar to a possible contact encounter with adjacently located tissue. The outer elements of the predetermined spatial geometry 103 are configured to provide a bumper (at least one or more bumpers) configured to prevent unwanted contact (physical contact) between the piercing stylet device 104 and the adjacently located tissue. In this arrangement, any adjacently located tissue is prevented (at least in part) from unwanted contact with the piercing stylet device 104 (that is, after the piercing stylet device 104 has punctured and travelled through the biological wall 906). It will be appreciated that in accordance with a preferred embodiment, spatial geometry 103 (shape or biased shape) of the flexible distal shaft section 102 may also be arranged in a manner in which a straight line cannot be drawn from the piercing stylet device 104 without also contacting another part of the predetermined spatial geometry 103.

In accordance with the embodiment as depicted in FIG. 7, the piercing stylet device 104 points parallel to the biological wall 906 once the flexible distal shaft section 102 has been removed from the elongated interior channel 900 of the guidewire introducer 902 that is depicted in FIG. 4).

In accordance with the embodiment as depicted in FIG. 8, the piercing stylet device 104 points inwardly (that is, toward a portion of the predetermined spatial geometry 103) once the flexible distal shaft section 102 has been removed from the elongated interior channel 900 of the guidewire introducer 902 that is depicted in FIG. 4.

FIG. 9 depicts a top view of an embodiment of the medical guidewire assembly 100 of FIG. 7 (or FIG. 8).

Referring to the embodiment as depicted in FIG. 9, the predetermined spatial geometry 103 is formed on a plane (shown as a line in the top view of the embodiment of FIG. 9) once the flexible distal shaft section 102 is removed, at least in part, from the elongated interior channel 900 of the guidewire introducer 902.

Figures 10, 11:
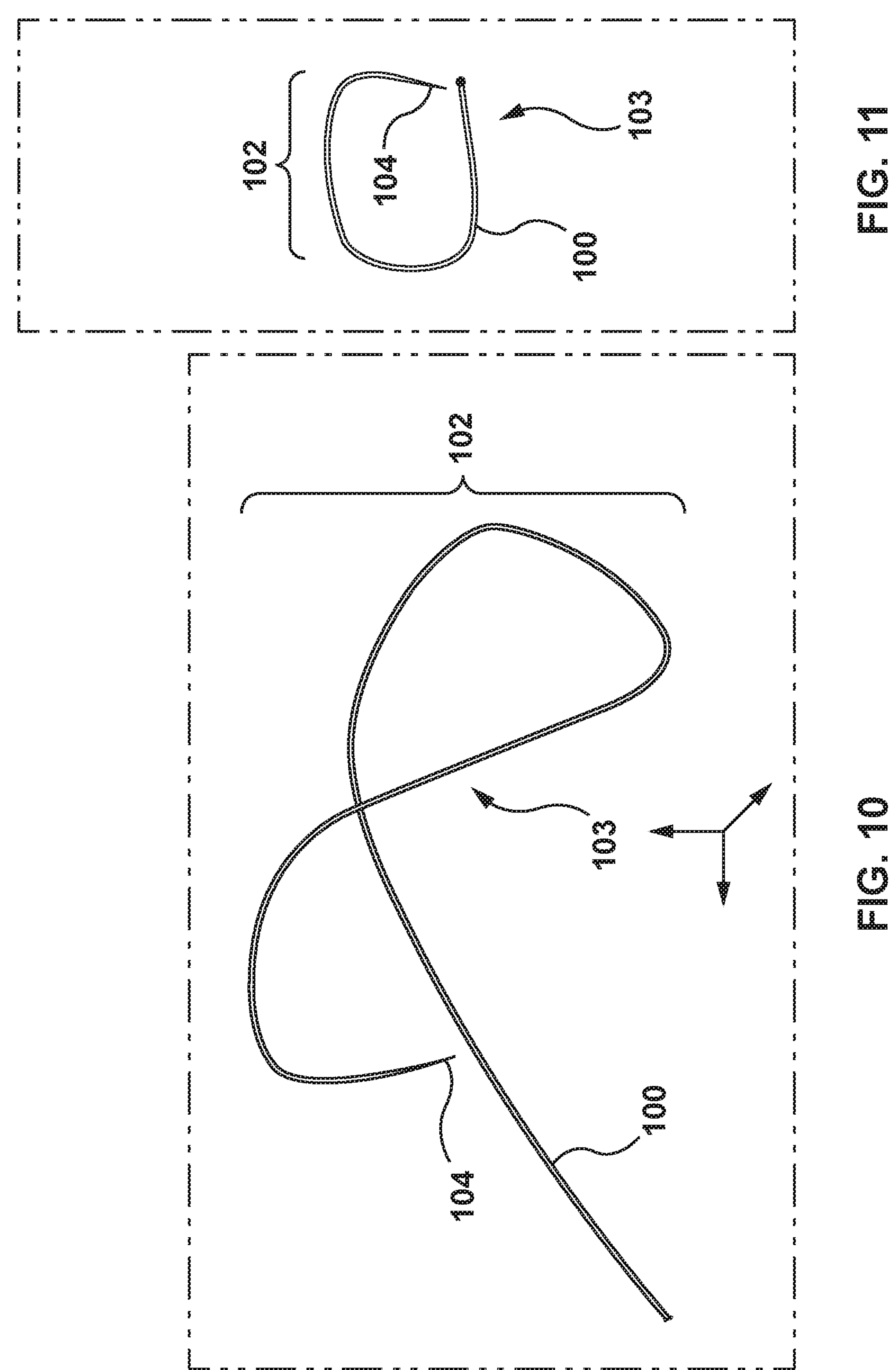
FIG. 10 (SHEET 4 of 5 SHEETS) depicts a side perspective view of an embodiment of the medical guidewire assembly of FIG. 4.
FIG. 11 (SHEET 4 of 5 SHEETS) depicts a top view of an embodiment of the medical guidewire assembly of FIG. 10.

FIG. 10 depicts a side perspective view of an embodiment of the medical guidewire assembly 100 of FIG. 4.

Referring to the embodiment as depicted in FIG. 10, the predetermined spatial geometry 103 is configured to span (form) into a three-dimensional formation once the flexible distal shaft section 102 is removed, at least in part, from the elongated interior channel 900 of the guidewire introducer 902. Alternatively, the predetermined spatial geometry 103 may span (form) into a single two-dimensional plane as depicted in the embodiment of FIG. 4. For the case where the predetermined spatial geometry 103 is configured to span (form) into the three-dimensional space, the predetermined spatial geometry 103 is configured to protect (guard) the piercing stylet device 104 from unwanted physical contact between the piercing stylet device 104 and the adjacently positioned tissue (once the piercing stylet device 104 is made to pass through the biological wall 906, and the flexible distal shaft section 102 becomes relaxed when removed from the elongated interior channel 900 of the guidewire introducer 902 to form the predetermined spatial geometry 103). The piercing stylet device 104 points toward a portion of the flexible distal shaft section 102 in the relaxed condition (relaxed state) as depicted in the embodiment of FIG. 10.

FIG. 11 depicts a top view of an embodiment of the medical guidewire assembly 100 of FIG. 10.

Referring to the embodiment as depicted in FIG. 11, the predetermined spatial geometry 103 forms a square-shaped formation (which is a projection taken from the top view of the embodiment of FIG. 10).

FIG. 12, FIG. 13, FIG. 14, FIG. 15 and FIG. 16 depict side views of embodiments of the medical guidewire assembly 100 of FIG. 4.

In accordance with the embodiments as depicted in FIG. 12 to FIG. 16, the flexible distal shaft section 102 may include various arrangements or spatial geometries configured to position the piercing stylet device 104 in a non-contacting spatial relationship with any adjacently positioned tissue of the patient (that is, once the predetermined spatial geometry 103 is formed as a result of removing the flexible distal shaft section 102 from elongated interior channel 900 of the guidewire introducer 902, which is depicted in any of FIG. 1 to FIG. 4).

Figures 12, 13:
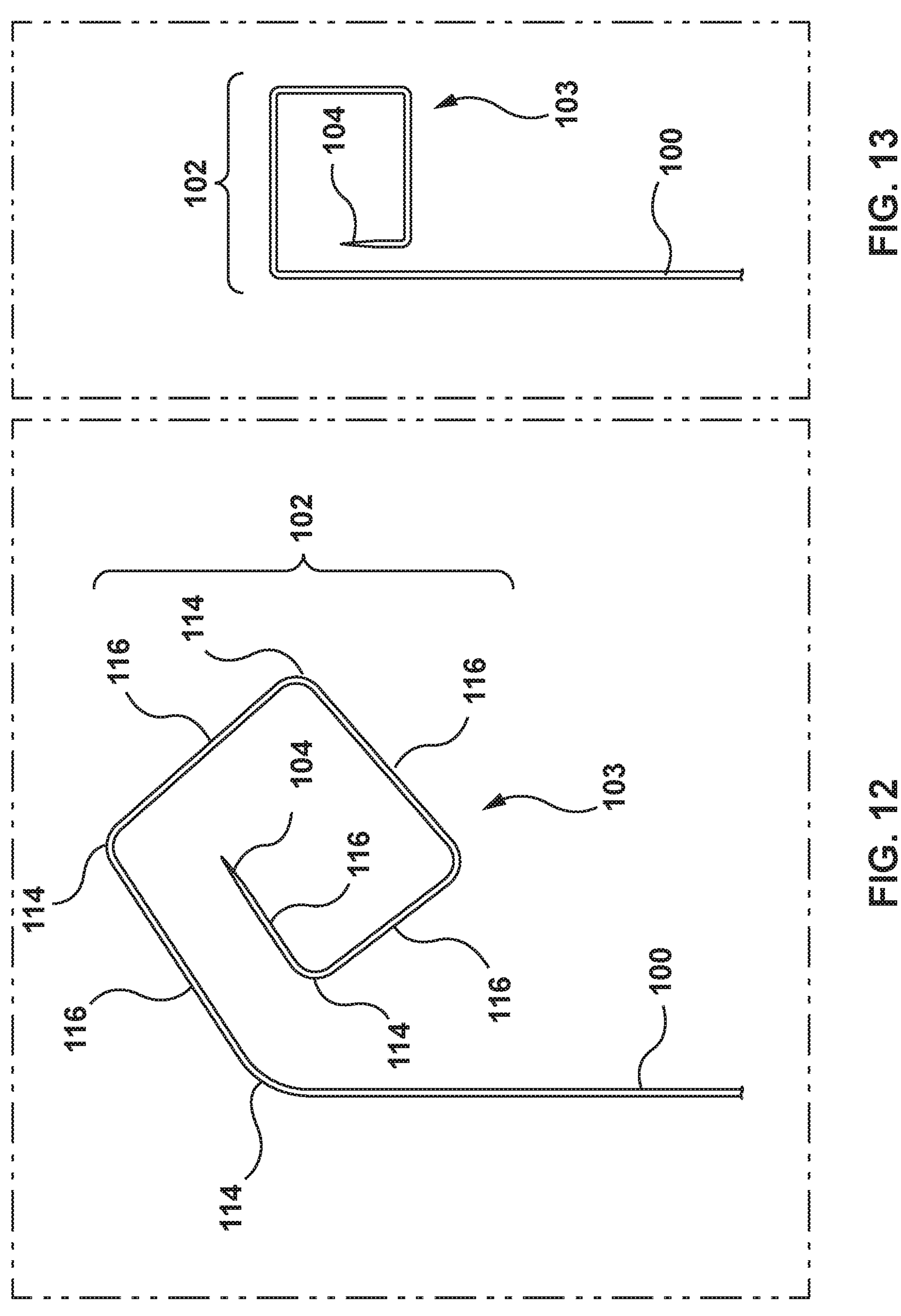
FIG. 12, FIG. 13, FIG. 14, FIG. 15 and FIG. 16 (SHEET 5 of 5 SHEETS) depict side views of embodiments of the medical guidewire assembly of FIG. 4.

In accordance with the embodiment as depicted in FIG. 12, the flexible distal shaft section 102 includes rigid spaced-apart members 116 (also called relatively stiffer sections or elongated sections). The rigid spaced-apart members 116 are separated by spaced-apart articulation points 114 (also called articulation points). In the relaxed configuration (that is, once the flexible distal shaft section 102 is removed, at least in part, from the guidewire introducer 902), the articulation points 114 are configured to align (move, position) the rigid spaced-apart members 116 into a relatively parallel-shaped configuration (that is, once the flexible distal shaft section 102 is removed, at least in part, from the guidewire introducer 902). The articulation points 114 are configured to facilitate or permit movement of the rigid spaced-apart members 116 in such a way that the predetermined spatial geometry 103 forms a distal configuration configured to prevent unwanted physical contact between the piercing stylet device 104 and any adjacently located tissue. Generally, in accordance with the embodiment as depicted in FIG. 12, the flexible distal shaft section 102 includes a relatively stiffer member 116 positioned between a pair of spaced-apart articulation points 114.

In accordance with the embodiment as depicted in FIG. 13, the predetermined spatial geometry 103 includes a square-shaped geometry (that is, once the flexible distal shaft section 102 is removed, at least in part, from the guidewire introducer 902).

Figures 14, 15, 16:
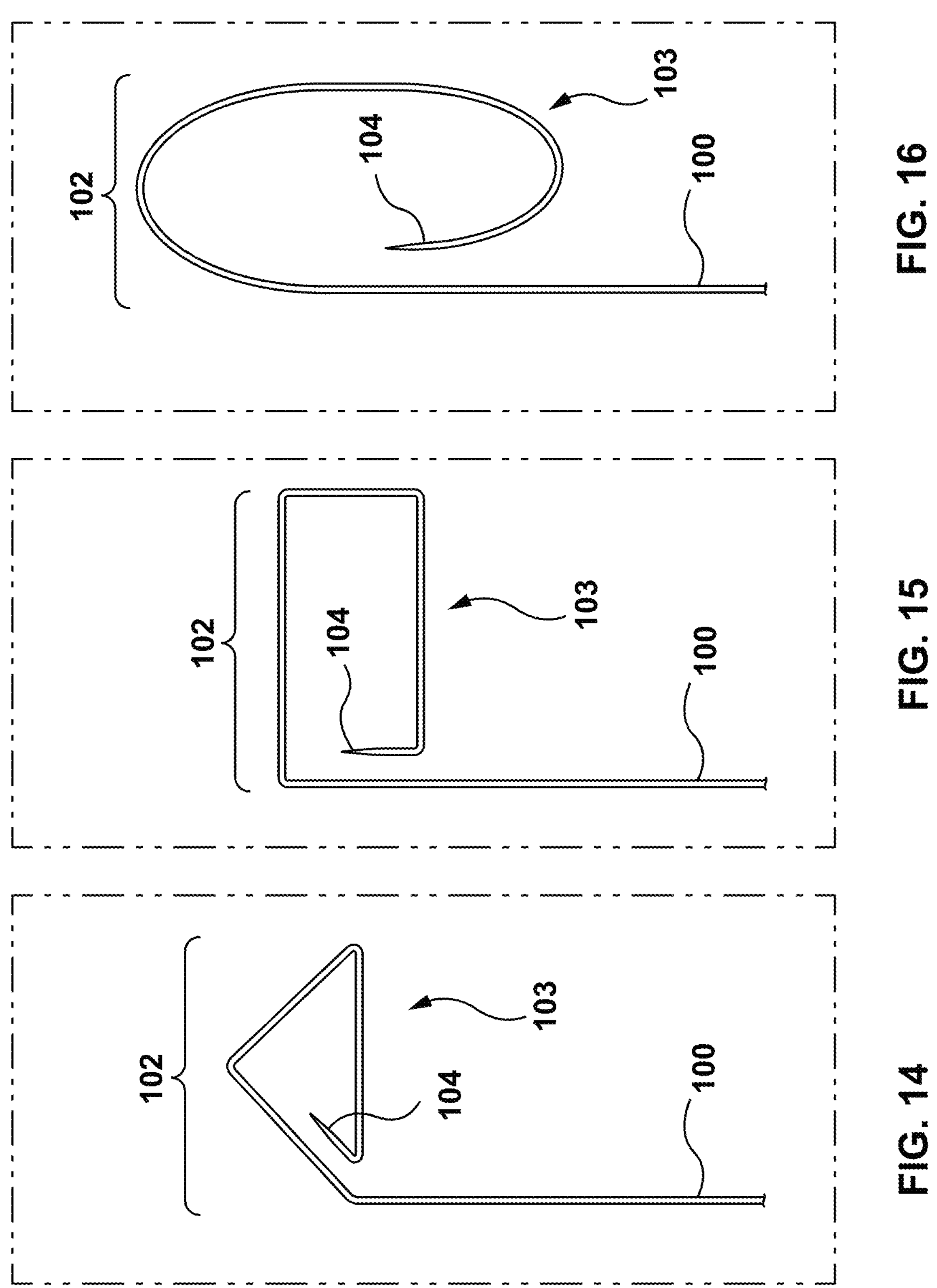

In accordance with the embodiment as depicted in FIG. 14, the predetermined spatial geometry 103 includes a triangular-shaped geometry (that is, once the flexible distal shaft section 102 is removed, at least in part, from the guidewire introducer 902).

In accordance with the embodiment as depicted in FIG. 15, the predetermined spatial geometry 103 includes a rectangular-shaped geometry (that is, once the flexible distal shaft section 102 is removed, at least in part, from the guidewire introducer 902).

In accordance with the embodiment as depicted in FIG. 16, the predetermined spatial geometry 103 includes an oval-shaped geometry (that is, once the flexible distal shaft section 102 is removed, at least in part, from the guidewire introducer 902).

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the invention which does not materially modify the invention. Similarly, unless specifically made clear from its context, numerical values should be construed to include certain tolerances that the person skilled in the art would recognize as having negligible importance as they do not materially change the operability of the invention. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options would be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the invention. The foregoing has outlined the non-limiting embodiments (examples). The description is made for particular non-limiting embodiments (examples). It is understood that the non-limiting embodiments are merely illustrative as examples.

What is claimed is:

1. An apparatus, comprising:

a medical guidewire assembly configured to be movable, at least in part, through an exit portal of a guidewire introducer, and the exit portal being in fluid communication with an elongated interior channel extending, at least in part, longitudinally along the guidewire introducer, and the exit portal being positionable proximate to a biological wall located within the body of a patient; and the medical guidewire assembly having a flexible distal shaft section; and the flexible distal shaft section being configured to extend, at least in part, longitudinally along the elongated interior channel of the guidewire introducer after the flexible distal shaft section is received in, and supported by, the elongated interior channel; and the flexible distal shaft section also being configured to have a predetermined spatial geometry once the flexible distal shaft section is moved beyond said exit portal, at least in part, from, and unsupported by, the elongated interior channel of the guidewire introducer, wherein the flexible distal shaft section includes a shaft guard portion spaced apart from the piercing stylet device, the shaft guard portion being configured to shield the piercing stylet device when the predetermined spatial geometry is formed; and the medical guidewire assembly having a piercing stylet device extending from the flexible distal shaft section; and the piercing stylet device being configured to puncture the biological wall of the patient in response to placement of the exit portal of the guidewire introducer, in use, proximate to the biological wall of the patient, and movement of the flexible distal shaft section through the exit portal toward the biological wall; and the predetermined spatial geometry of the flexible distal shaft section being configured to prevent, at least in part, physical contact between the piercing stylet device and adjacently positioned tissue of the patient in response to formation of the predetermined spatial geometry by further movement of the flexible distal shaft section through the exit portal of the guidewire introducer after the biological wall is punctured by the piercing stylet device, wherein the predetermined spatial geometry forms a closed loop arrangement and causes the piercing stylet device to make physical contact with the shaft guard portion.

2. The apparatus of claim 1, wherein:

the shaft guard portion is configured to shield the piercing stylet device in response to formation of the predetermined spatial geometry by further movement of the flexible distal shaft section through the exit portal of the guidewire introducer after the biological wall is punctured by the piercing stylet device in such a way that the shaft guard portion, in use, prevents contact between the piercing stylet device and adjacently positioned tissue of the patient.

3. The apparatus of claim 1, wherein:

the flexible distal shaft section is configured to become fully relaxed and unsupported by the elongated interior channel of the guidewire introducer in response to progress of the flexible distal shaft section beyond the exit portal, from the elongated interior channel.

4. The apparatus of claim 1, wherein:

the predetermined spatial geometry is configured to be biased to lie on, and extend along, a single planar surface in response to progress of the flexible distal shaft section beyond the exit portal, from the elongated interior channel.

5. The apparatus of claim 1, wherein:

the flexible distal shaft section is configured to articulate to form the predetermined spatial geometry once the flexible distal shaft section is moved beyond the exit portal of the guidewire introducer.

6. The apparatus of claim 1, wherein:

the flexible distal shaft section has an inherent flexible tendency to become formed into the predetermined spatial geometry once the flexible distal shaft section is moved beyond the exit portal, at least in part, of the guidewire introducer.

7. The apparatus of claim 1, wherein:

the predetermined spatial geometry maintains the piercing stylet device and adjacently positioned tissue of the patient in a non-contact relationship with each other, and once the predetermined spatial geometry becomes formed, the predetermined spatial geometry prevents, at least in part, physical contact between the piercing stylet device and adjacently positioned tissue of the patient.

8. The apparatus of claim 1, wherein:

the piercing stylet device is positionable fully inside the left atrium of the patient; and the predetermined spatial geometry is in a relaxed configuration in such a way that the predetermined spatial geometry of the flexible distal shaft section, in use, prevents physical contact between the piercing stylet device and any adjacently positioned tissue.

9. The apparatus of claim 1, wherein:

the predetermined spatial geometry is sized to fit in the left atrium of the heart.

10. The apparatus of claim 1, wherein:

the predetermined spatial geometry is formed such that the piercing stylet device is positioned within a confine of the predetermined spatial geometry and is surrounded by the predetermined spatial geometry.

11. The apparatus of claim 1, wherein:

the predetermined spatial geometry is configured in a way that a straight line cannot be drawn to the piercing stylet device without first contacting another portion of the predetermined spatial geometry of the flexible distal shaft section.

12. The apparatus of claim 1, wherein:

the predetermined spatial geometry forms the closed loop arrangement configured to prevent a straight line from being drawn to the piercing stylet device without first contacting another portion of the predetermined spatial geometry.

13. The apparatus of claim 1, wherein:

the predetermined spatial geometry is formed on a plane once the flexible distal shaft section is moved beyond the exit portal, at least in part, of the guidewire introducer.

14. The apparatus of claim 1, wherein:

the predetermined spatial geometry is configured to form into a three-dimensional formation once the flexible distal shaft section is moved beyond the exit portal, at least in part, of the guidewire introducer.

15. The apparatus of claim 1, wherein:

the predetermined spatial geometry is configured to span into a three-dimensional formation having a square-shaped formation with the piercing stylet pointing towards a shaft guard portion.

16. An apparatus, comprising:

a medical guidewire assembly configured to be movable, at least in part, through an exit portal of a guidewire introducer, and the exit portal being in fluid communication with an elongated interior channel extending, at least in part, longitudinally along the guidewire introducer, and the exit portal being positionable proximate to a biological wall located within the body of a patient; and the medical guidewire assembly having a flexible distal shaft section; and the flexible distal shaft section being configured to extend, at least in part, longitudinally along the elongated interior channel of the guidewire introducer after the flexible distal shaft section is received in, and supported by, the elongated interior channel; and the flexible distal shaft section also being configured to have a predetermined spatial geometry once the flexible distal shaft section is moved beyond said exit portal, at least in part, from, and unsupported by, the elongated interior channel of the guidewire introducer, wherein the flexible distal shaft section includes a shaft guard portion spaced apart from the piercing stylet device, the shaft guard portion being configured to shield the piercing stylet device when the predetermined spatial geometry is formed; and the medical guidewire assembly having a piercing stylet device extending from the flexible distal shaft section; and the piercing stylet device being configured to puncture the biological wall of the patient in response to placement of the exit portal of the guidewire introducer, in use, proximate to the biological wall of the patient, and movement of the flexible distal shaft section through the exit portal toward the biological wall; and the predetermined spatial geometry of the flexible distal shaft section being configured to prevent, at least in part, physical contact between the piercing stylet device and adjacently positioned tissue of the patient in response to formation of the predetermined spatial geometry by further movement of the flexible distal shaft section through the exit portal of the guidewire introducer after the biological wall is punctured by the piercing stylet device, wherein the predetermined spatial geometry forms a closed loop arrangement and causes the piercing stylet device to make physical contact with the shaft guard portion;

wherein the predetermined spatial geometry forms the closed loop arrangement configured to prevent a straight line from being drawn to the piercing stylet device without first contacting another portion of the predetermined spatial geometry.

17. The apparatus of claim 16, wherein the flexible distal shaft section is configured to become fully relaxed and unsupported by the elongated interior channel of the guidewire introducer in response to progress of the flexible distal shaft section beyond the exit portal, from the elongated interior channel.

18. The apparatus of claim 17, wherein the predetermined spatial geometry is configured to be biased to lie on, and extend along, a single planar surface in response to progress of the flexible distal shaft section beyond the exit portal, from the elongated interior channel.

19. The apparatus of claim 18, wherein the piercing stylet device is positionable fully inside the left atrium of the patient; and the predetermined spatial geometry is in a relaxed configuration in such a way that the predetermined spatial geometry of the flexible distal shaft section, in use, prevents physical contact between the piercing stylet device and any adjacently positioned tissue.

20. The apparatus of claim 17, wherein the predetermined spatial geometry is configured to span into a three-dimensional formation having a square-shaped formation with the piercing stylet pointing towards the shaft guard portion.

* * * * *